United States Patent
Maracas et al.

[11] Patent Number: 5,954,931
[45] Date of Patent: Sep. 21, 1999

[54] ELECTROPHORESIS APPARATUS AND METHOD INVOLVING PARALLEL CHANNELS

[75] Inventors: George N. Maracas, Phoenix, Ariz.; William L. Reber, Schaumburg, Ill.; Cary D. Perttunen, Shelby Township, Mich.

[73] Assignee: Motorola, Inc., Schaumburg, Ill.

[21] Appl. No.: 08/788,612

[22] Filed: Jan. 24, 1997

[51] Int. Cl.⁶ .......................... G01N 27/26; G01N 27/447
[52] U.S. Cl. .......................... 204/451; 204/452; 204/453; 204/601; 204/603; 204/604
[58] Field of Search ................... 204/451–455, 204/601–605, 450, 600

[56] References Cited

U.S. PATENT DOCUMENTS

| | | |
|---|---|---|
| 3,620,958 | 11/1971 | Dijksterhuis et al. . |
| 3,941,678 | 3/1976 | Akiyama . |
| 4,118,280 | 10/1978 | Charles et al. . |
| 4,898,658 | 2/1990 | Karger et al. . |
| 5,096,670 | 3/1992 | Harris et al. . |
| 5,139,744 | 8/1992 | Kowalski . |
| 5,429,734 | 7/1995 | Gajar et al. . |
| 5,518,923 | 5/1996 | Berndt et al. . |
| 5,532,128 | 7/1996 | Eggers et al. . |
| 5,565,324 | 10/1996 | Still et al. . |
| 5,599,432 | 2/1997 | Manz et al. . |
| 5,653,939 | 8/1997 | Hollis et al. . |
| 5,661,028 | 8/1997 | Foote . |
| 5,736,332 | 4/1998 | Mandecki . |

FOREIGN PATENT DOCUMENTS 0 620 432  10/1994  European Pat. Off. .

OTHER PUBLICATIONS

Woolley et al. "Ultra–high–speed DNA fragment separations using microfabricated capillary array electrophoresis chips." Proc. Natl. Acad. Sci. vol. 91 (Nov. 1994), pp. 11348–11352.
www.labfocus.com/biochem/labfeat.htm (No Date Provided).
www.labfocus.com/abc/STAFEA.htm (No Date Provided).
www.awaretech.com/Identi–Link.html (No Date Provided).
www.labfocus.com/biochem/labotech.htm (No Date Provided).
www.sanguin.com/M2000.HTM (No Date Provided).
www.sanguin.com/INFORM.HTM (No Date Provided).
www.packardinst.com/m–probe.htm (No Date Provided).
www.packardinst.com/mp204–bc.htm (No Date Provided).
"Advances in Microfabrication Devices Lead to Innovation in Electrophoresis", Genetic Engineering News, Sep. 15, 1996, pp. 18–19.
"Complex Optical Surfaces Formed by Replica Molding Against Elastomeric Masters", Science, vol. 273, pp. 347, Jul. 19, 1996.

*Primary Examiner*—William H. Beisner

[57] ABSTRACT

An electrophoresis apparatus includes a substrate (34) which supports a filling region (22) and a plurality of electrophoresis lanes (20). The filling region (22) communicates a sample to the plurality of electrophoresis lanes (20). A method of electrophoresis includes providing the above-described electrophoresis apparatus, applying a sample to the filling region (22), the plurality of electrophoresis lanes (20) receiving the sample from the filling region (22), and electrophoresing the sample in the plurality of electrophoresis lanes (20).

21 Claims, 11 Drawing Sheets

ELECTROPHORESIS APPARATUS AND METHOD INVOLVING PARALLEL CHANNELS

RELATED APPLICATION

The present application is related to the following applications:

"Methods and Systems for Biological Reagent Placement", having Ser. No. 08/648,635, filed on May 13, 1996, now U.S. Pat. No. 5,731,152;

"Automated Electrophoresis System and Method", having Ser. No. 08/788,970, MNE00503 filed on Jan. 24, 1997, now U.S. Pat. No. 5,851,370; and "Assay Dispensing Apparatus", having Ser. No. 08/789,220, MNE00502 filed on Jan. 24, 1997, now U.S. Pat. No. 5,772,966.

The subject matter of the above-identified related applications is hereby incorporated by reference into the disclosure of this application.

FIELD OF THE INVENTION

The present invention relates to electrophoresis devices and methods.

BACKGROUND OF THE INVENTION

Gel electrophoresis devices commonly include a sheet or slab of gel material sandwiched between two glass plates. A comb is utilized to form a plurality of sample wells in the gel. Each sample well corresponds to a single electrophoresis lane.

A respective sample is loaded into each sample well. Thereafter, a voltage is applied across the gel to generate an electric field to simultaneously electrophorese all of the samples. As the samples migrate in the gel due to the electric field, there is a potential for interaction or bleeding between adjacent lanes that are closely positioned. The potential for interaction limits a number of physical lanes which can be provided using this approach.

BRIEF DESCRIPTION OF THE DRAWINGS

The invention is pointed out with particularity in the appended claims. However, other aspects of the present invention are disclosed in the following detailed description and the accompanying drawings in which:

DETAILED DESCRIPTION OF A PREFERRED EMBODIMENT

Figure 1:
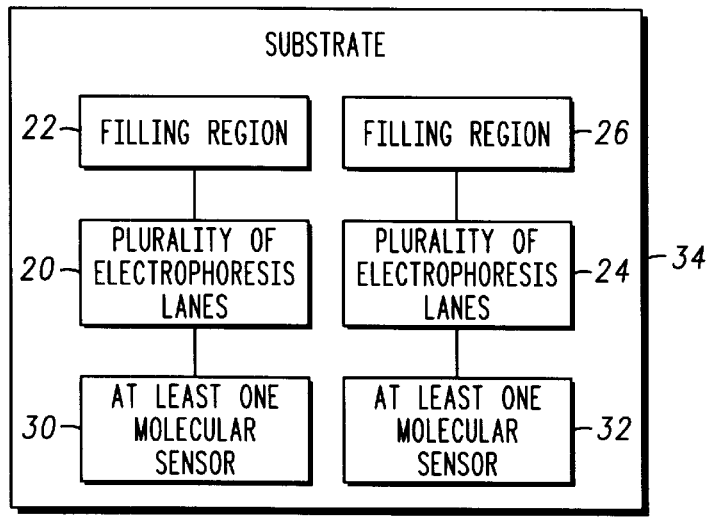
FIG. 1 is a block diagram of a first embodiment of an electrophoresis device in accordance with the present invention.

FIG. 1 is a block diagram of a first embodiment of an electrophoresis device in accordance with the present invention. The electrophoresis device includes a first plurality of electrophoresis lanes 20 in communication with a first filling region 22. The first filling region 22 is utilized to receive a first sample of molecules for separation in each of the first plurality of electrophoresis lanes 20. The first sample can be separated in the first plurality of electrophoresis lanes 20 using an electrophoresis process, such as a gel electrophoresis process or a capillary electrophoresis process which are known in the art.

It is noted that the term "sample" in the present application is inclusive of a variety of samples, including but not limited to medical samples, genomic samples, environmental samples, and agricultural samples. Of particular interest is a sample having molecular chains of at least one nucleotide. Here, for example, the sample can include a processed DNA sample or a processed RNA sample from a plant or a living organism, such as a human. In these applications, the sample typically includes a plurality of fragments of DNA or RNA formed using a restriction enzyme.

Optionally, the molecules in the sample are tagged with a member which can be sensed by a molecular sensor. Such members are commonly referred to in the art as tags, markers, reporters, and labels. Examples of such members include, but are not limited to, radioactive members, optical members (such as fluorescent members, luminescent members, and light-scattering members), charged members, and magnetic members.

By electrophoresing the sample, one or more characteristics of molecules contained in the sample can be determined. For example, the sample can be electrophoresed to detect a predetermined molecular structure in the sample. The predetermined molecular structure can indicate, for example: (i) the presence of a pathogen in an environmental sample such as water; (ii) crop resistance in an agricultural sample; or (iii) a disease gene in a medical sample. Alternatively, the sample can be electrophoresed to determine a molecular structure associated with the sample. Here, for example, the sample is electrophoresed to determine a nucleotide base sequence associated therewith. As another alternative, the sample can be electrophoresed in a fragment sizing application.

The electrophoresis device can also include a second plurality of electrophoresis lanes 24 in communication with a second filling region 26. The second filling region 26 is utilized to receive a second sample of molecules for separation in each of the second plurality of electrophoresis lanes 24. The second sample can be separated in the second plurality of electrophoresis lanes 24 in the same manner as the first sample.

Preferably, the electrophoresis device provides a physical barrier between the combination of the first plurality of electrophoresis lanes 20 and the first filling region 22, and the combination of the second plurality of electrophoresis lanes 24 and the second filling region 26. As a result, communication of the first sample to the second plurality of electrophoresis lanes 24 or to the second filling region 26 is inhibited. Similarly, communication of the second sample to the first plurality of electrophoresis lanes 20 or to the first filling region 22 is inhibited.

In general, the electrophoresis device can include any number of filling regions rather than just the two described above. Further, each filling region can have any respective plurality of electrophoresis lanes in communication therewith. Depending on the size of the device and the width of the lanes, the device can define hundreds of lanes, thousands of lanes, tens of thousands of lanes, or hundreds of thousands of lanes. Regardless of the number of lanes, the electrophoresis device can provide physical barriers, as described earlier, which inhibit cross contamination of samples between predetermined pairs of lanes.

The electrophoresis device further comprises at least one molecular sensor 30 associated with the first plurality of electrophoresis lanes 20 to sense molecules which pass by its location during electrophoresis. Examples of the at least one molecular sensor 30 include, but are not limited to, an optical sensor, an electrical sensor, and a radioactive sensor. The at least one molecular sensor 30 may directly sense untagged molecules or indirectly sense molecules by sensing the tagging members associated therewith.

As is known in the art, the process of electrophoresis separates the sample of molecules in dependence upon the size of the molecules. In many applications, a number of bands of like-sized molecules are formed during electrophoresis. In these applications, each of the at least one molecular sensor 30 senses bands of like-sized molecules which pass thereby.

Preferably, the at least one molecular sensor 30 includes at least one molecular sensor for each of the first plurality of electrophoresis lanes 20. If desired, the at least one molecular sensor 30 can include a plurality of molecular sensors distributed along each electrophoresis lane. It is also preferred that each of the at least one molecular sensor 30 has a fixed position and/or location along its respective electrophoresis lane.

The electrophoresis device further comprises at least one molecular sensor 32 associated with the second plurality of electrophoresis lanes 24. Preferably, the at least one molecular sensor 32 includes at least one molecular sensor for each of the second plurality of electrophoresis lanes 24. If desired, the at least one molecular sensor 32 can include a plurality of molecular sensors distributed along each electrophoresis lane. It is also preferred that each of the at least one molecular sensor 32 has a fixed position and/or location along its respective electrophoresis lane.

Each of the at least one molecular sensor 32 is utilized to sense molecules which pass by its location during electrophoresis. As with the at least one molecular sensor 30, each of the at least one molecular sensor 32 can be utilized to sense bands of like-sized molecules which pass thereby.

The first plurality of electrophoresis lanes 20, the first filling region 22, the second plurality of electrophoresis lanes 24, and the second filling region are supported by a substrate 34. In a preferred embodiment, the substrate 34 is micropatterned to define the first plurality of electrophoresis lanes 20, the first filling region 22, the second plurality of electrophoresis lanes 24, and the second filling region 26. Additionally, the at least one molecular sensor 30 and the at least one molecular sensor 32 can be integrated with the substrate 34, or can be external to the substrate 34.

Figure 2:
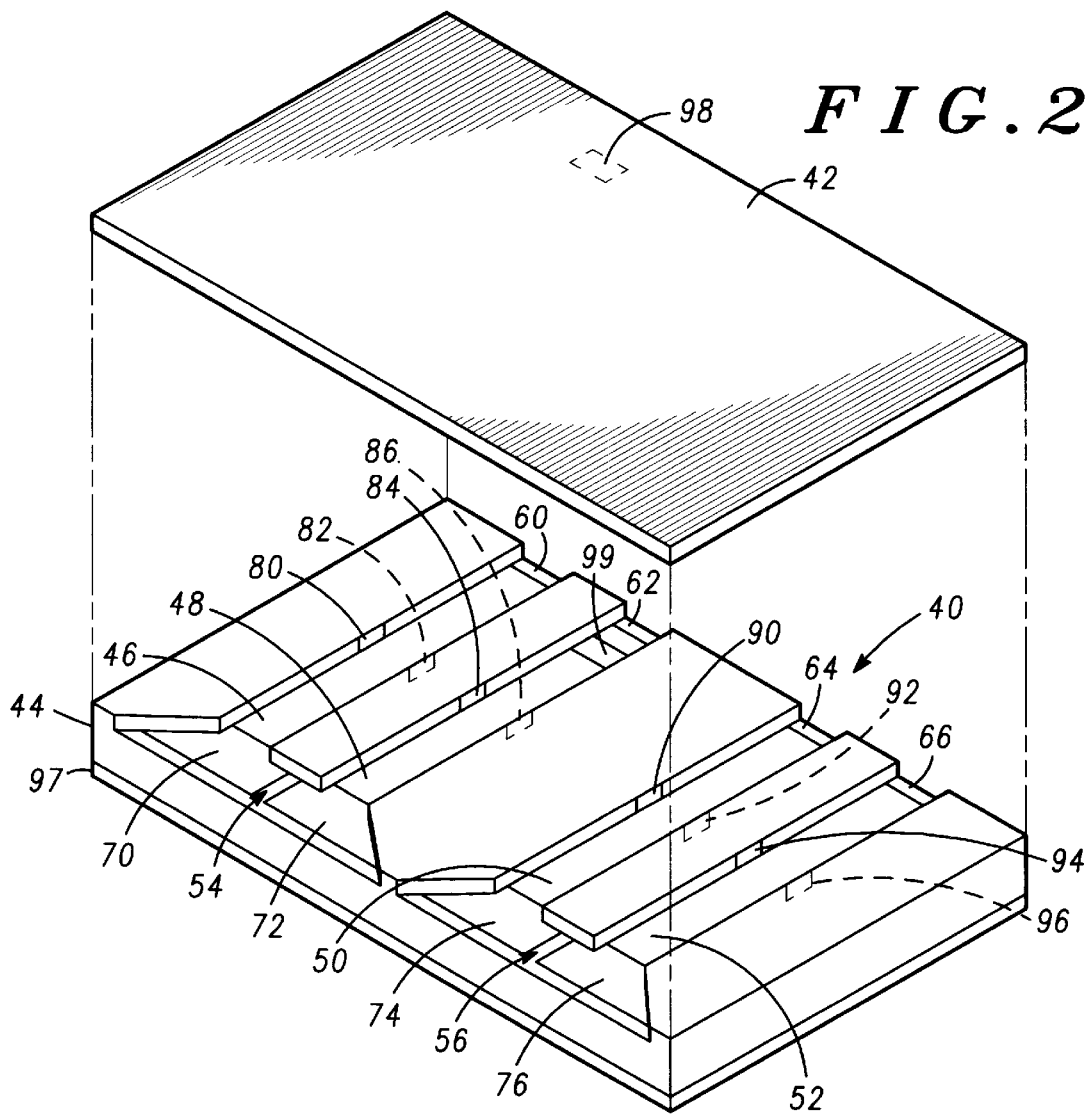
FIG. 2 is a perspective view of a second embodiment of an electrophoresis device in accordance with the present invention.

FIG. 2 is a perspective view of a second embodiment of an electrophoresis device in accordance with the present invention. The electrophoresis device includes a first plate 40 and a second plate 42. The first plate 40 includes a substrate 44 patterned to define a first plurality of channels or troughs, including channels 46 and 48, a second plurality of channels including channels 50 and 52, a first filling region 54, and a second filling region 56. The second plate 42 is utilized to cover a face of the first plate 40 at which the channels 46, 48, 50, and 52 and the filling regions 54 and 56 are defined.

The first plate 40 and the second plate 42 can be formed of materials including, but not limited to, insulator materials, semiconductor materials, glass, polymers, or plastic. The channels 46, 48, 50, and 52 and the filling regions 54 and 56 can be formed during molding of the substrate 44 or can be etched or machined into the substrate 44.

A suitable gel, such as an acrylamide gel or an agarose gel, is preferably cast into the channels 46, 48, 50, and 52. With the second plate 42 removed from the first plate 40, the channels 46, 48, 50, and 52 can be filled with the gel using a doctor blade or a similar technique. Thereafter, the second plate 42 is secured over the first plate 40 to enclose the gel within the channels 46, 48, 50, and 52. Alternatively, the channels 46, 48, 50, and 52 can be filled with the gel while the second plate 42 is secured over the first plate 40. In this case, the gel can be pumped through the channels 46, 48, 50, 52, or can be drawn through the channels 46, 48, 50, and 52 using a vacuum.

With the second plate 42 covering the first plate 40, a first sample of molecules is applied to the first filling region 54 and a second sample of molecules is applied to the second filling region 56. The first filling region 54 communicates the first sample to the first plurality of channels, including the channels 46 and 48. The first plurality of channels provides a first plurality of electrophoresis lanes for the first sample. The second filling region 56 communicates the second sample to the second plurality of channels, including the channels 50 and 52. The second plurality of channels provides a second plurality of electrophoresis lanes for the second sample.

Associated with each channel is a pair of electrodes for generating an electric field therein. With reference to the embodiment illustrated in FIG. 2, electrodes 60, 62, 64, and 66 are integrated with the substrate 44 at a terminal end of the channels 46, 48, 50, and 52, respectively. Electrodes 70, 72, 74, and 76 are integrated with the substrate 44 near a sample-receiving end of the channels 46, 48, 50, and 52, respectively. As illustrated, portions of the electrodes 70 and 72 can be located at the first filling region 54, and portions of the electrodes 74 and 76 can be located at the second filling region 56. If desired, the electrodes 70 and 72 can be merged as a single electrode, and the electrodes 74 and 76 can be merged as a single electrode. The electrodes 60, 62, 64, 66, 70, 72, 74, and 76 can be formed of a semiconductor material or a conductor material, such as a metal or a polymer, integrated with the substrate 44.

An electric field is generated in a channel by applying a voltage across its associated pair of electrodes. For example, an electric field is generated in the channel 46 by applying a voltage between the electrode 70 and the electrode 60. The electric field is applied to electrophorese the samples in the filling regions.

By including a respective pair of electrodes for each channel, the electric field in each channel can be independently controlled. This configuration affords the flexibility of: (i) applying a common electric field to all of the channels; (ii) applying a common electric field to all channels in communication with a common filling region, with the possibility of applying a different electric field to channels in communication with a different filling region; or (iii) applying a different electric field to different channels associated with a common filling region.

To sense molecular transport induced by the electric field, a pair of sensing electrodes is associated with each channel. With reference to the embodiment illustrated in FIG. 2, a first electrode 80 and a second electrode 82 are proximate to the channel 46, a first electrode 84 and a second electrode 86 are proximate to the channel 48, a first electrode 90 and a second electrode 92 are proximate to the channel 50, and a first electrode 94 and a second electrode 96 are proximate to the channel 52. Each first electrode and second electrode are located at opposite sides along a width of its associated channel. Preferably, the electrodes 80, 82, 84, 86, 90, 92, 94, and 96 are formed of a semiconductor material or a conductor material, such as a metal or a polymer, integrated with the substrate 44.

If desired, each first electrode and second electrode can abut an interior of the channel to provide contact with the gel and/or the sample therein. Alternatively, each channel can have a first insulating layer and a second insulating layer which electrically insulates the first electrode and the second electrode, respectively, from the interior of the channel. The insulating layers can serve to capacitively couple the electrodes to the channel, and to protect the electrodes from corrosion.

Each pair of sensing electrodes performs an impedance measurement at a predetermined location in the channel. The impedance measurement is used to determine the presence of molecules from the sample at the location. Either a real part or an imaginary part of the impedance can be measured. Typically, the impedance varies from a nominal level as molecules from the sample become proximate to the sensing electrodes. The impedance can increase or decrease from the nominal level based upon the charged state of the molecules.

Optionally, the first plate 40 includes a heat sink 97 which draws heat generated during electrophoresis from the first plurality of channels and the second plurality of channels. Preferably, the heat sink 97 is integrated with the substrate 44 at an opposite face relative to the face at which the channels are defined.

The heat sink 97 acts to reduce temperature differences both between channels and within channels. By equalizing the temperature between channels, the channel-to-channel variability of electrophoretic transport of like molecules is reduced. By equalizing the temperature within a channel, substantially-linear bands of molecules are formed during electrophoresis.

The heat sink 97 can be formed of a thermally-conductive material to passively draw heat from the channels. Alternatively, the heat sink 97 can include a thermoelectric member which actively cools the channels in response to an electrical signal applied thereto.

As with the embodiment described with reference to FIG. 1, it is noted that the electrophoresis device of FIG. 2 can generally include any number of filling regions, rather than the two described, and any number of channels per filling region.

The second plate 42 can be a plate dedicated for covering the first plate 40, or can serve other purposes. For example, the second plate 42 can include one or more of the elements described for the first plate 40. Here, the second plate 42 can be stacked on top of the first plate 40 so that electrophoresis can be performed using both plates. In this way, any plurality of like plates can be stacked to perform electrophoresis.

Another purpose which can be served by the second plate 42 is to assist in sensing molecular transport in the first plate 40. Here, in general, the second plate 42 can include one or more molecular sensors for sensing the molecular transport. In one embodiment, the second plate 42 includes an electrode 98 which is located proximate to a channel when the second plate 42 covers the first plate 40. Molecular transport can be sensed by sensing an impedance between the electrode 98 and an electrode 99 associated with the first plate 40.

Figure 3:
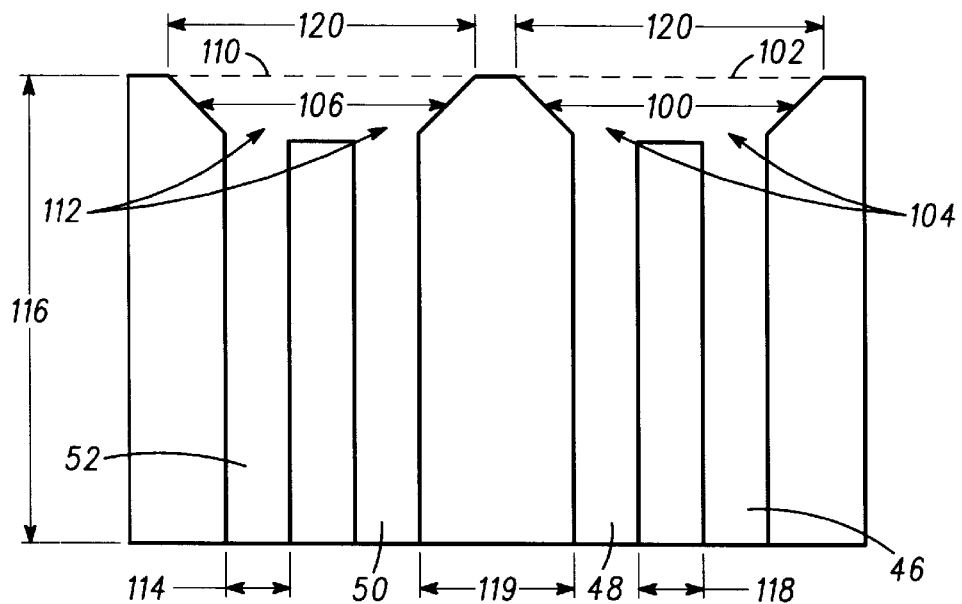
FIG. 3 is a sectional view of the first plate illustrated in FIG. 2.

FIG. 3 is a sectional view of the first plate 40 illustrated in FIG. 2. As illustrated, a dimension 100 of the first filling region 54 narrows from a sample-receiving opening 102 to openings 104 to the channels 46 and 48. Similarly, a dimension 106 of the second filling region 56 narrows from a sample-receiving opening 110 to openings 112 to the channels 50 and 52.

In general, the channels 46, 48, 50, and 52 and the filling regions 54 and 56 can be dimensioned and spaced as desired. Preferably, the filling regions 54 and 56 are dimensioned to have a predetermined volume. The predetermined volume is selected in accordance with a predetermined amount of sample which is to be applied to the channels.

In a preferred embodiment, each channel has a width 114 of 50 micrometers or less, a height of 50 micrometers or less, and a length 116, preferably between one and ten centimeters. A distance 118 between adjacent channels in communication with the same filling region is approximately the same as the width 114 of each channel. A distance 119 between adjacent channels in communication with different filling regions is greater than the width 114 of each channel.

The filling regions 54 and 56 each have a width 120 dependent upon the number of channels which communicate therewith and the dimensions of the channels. For two 50-micrometer channels per filling region, the cross-sectional width can be 250 micrometers or less. For three 50-micrometer channels per filling region, the width 120 can be 400 micrometers or less. In a preferred embodiment, the filling regions 54 and 56 have a height of 50 micrometers or less.

In general, the dimensions of the channels and the filling regions are selected with consideration to a resulting diffusion time of the molecules through the channels, and a resulting sensitivity for detecting bands of molecules using the electrodes 80, 82, 84, 86, 90, 92, 94, and 96.

Figure 4:
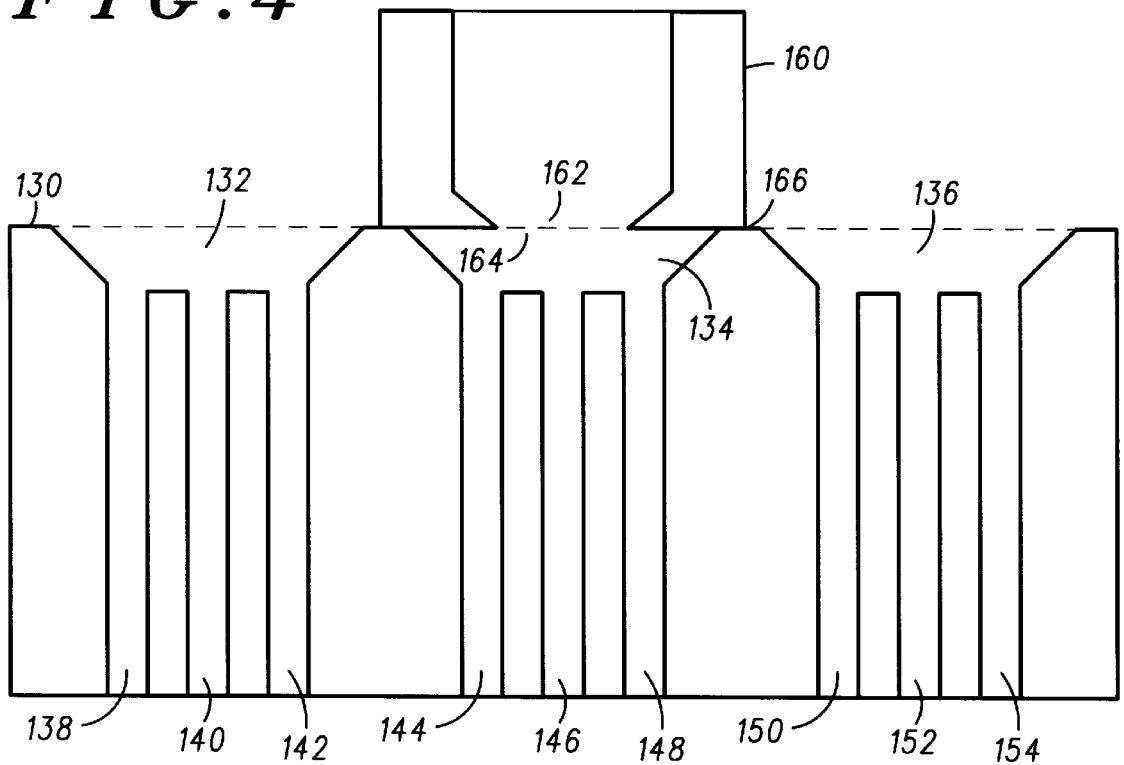
FIG. 4 is a cross-sectional view of a first embodiment of an apparatus for loading a sample into a third embodiment of an electrophoresis device.

FIG. 4 is a cross-sectional view of a first embodiment of an apparatus for loading a sample into a third embodiment of an electrophoresis device 130. The electrophoresis device 130 defines three filling regions 132, 134, and 136, and nine channels 138, 140, 142, 144, 146, 148, 150, 152, and 154, in a manner similar to the embodiment of FIGS. 2 and 3. The filling region 132 communicates a first sample received therein to the channels 138, 140, and 142. The filling region 134 communicates a second sample received therein to the channels 144, 146, and 148. The filling region 136 communicates a third sample received therein to the channels 150, 152, and 154.

The apparatus includes a gasket 160 for loading a sample into a filling region, such as loading the second sample into the filling region 134. A gasket 160 provides a terminal member of a sample dispensing apparatus such as a syringe or a sample handling robot. Preferably, the gasket 160 is formed of an elastomeric material such as teflon or rubber.

The gasket 160 defines an opening 162 through which the second sample is loaded into the filling region 134. The opening 162 is dimensioned to be smaller than an opening 164 of the filling region 134. An outer periphery 166 of the gasket 160 is dimensioned to fully surround the opening 164 of the filling region 134. When forced into contact with the electrophoresis device 130, the gasket 160 seals the filling region 134 from adjacent filling regions, namely the filling region 132 and the filling region 136, and from an external environment. Once sealed, the sample can be injected into the filling region 134 by pressurization. When the filling region 134 becomes filled with the sample, the gasket 160 is removed from the electrophoresis device.

The gasket 160 is advantageous in: (i) confining the sample to the filling region of interest; (ii) inhibiting the sample from contaminating adjacent filling regions; and (iii) dispensing a predetermined volume of sample based upon the volume of the filling region of interest. In addition, by utilizing filling regions which are significantly wider (e.g. 400 micrometers) than the channels (e.g. 50 micrometers), placement tolerances for the gasket 160 are relaxed and cross contamination of samples is reduced.

Figure 5:
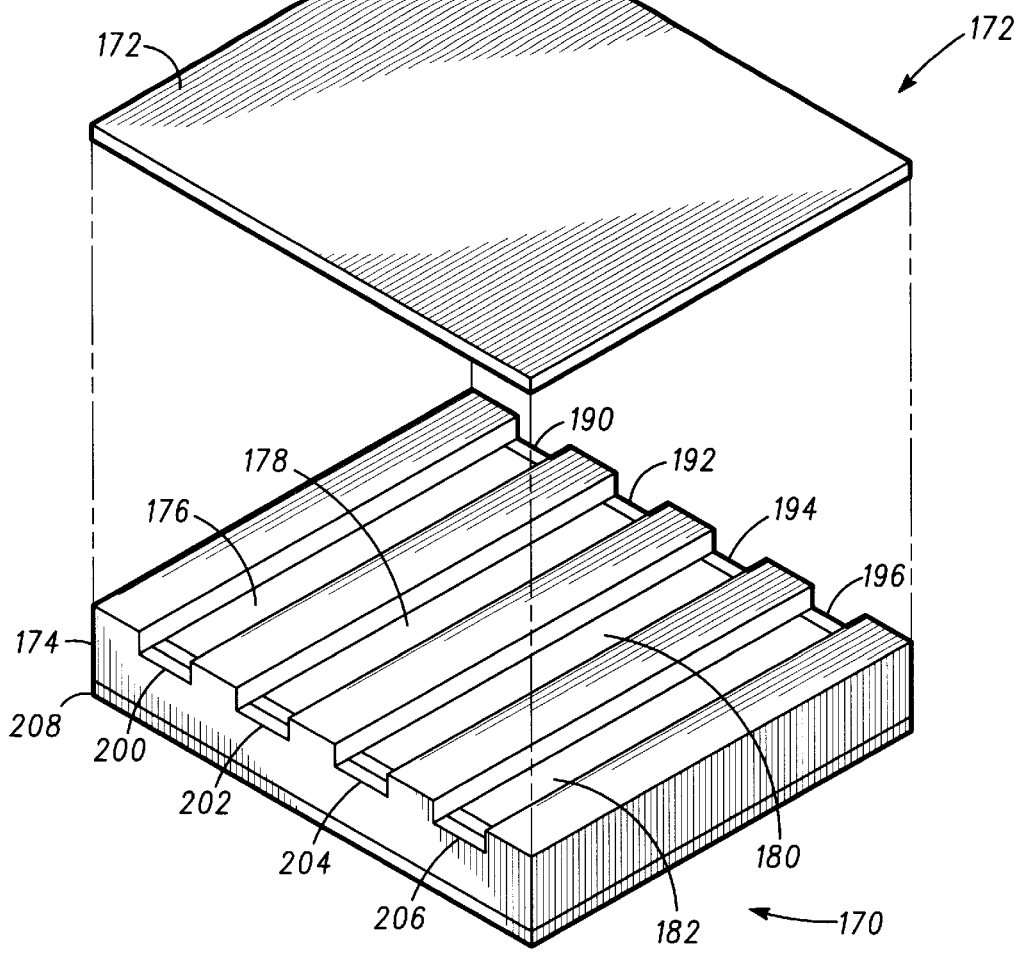
FIG. 5 is a perspective view of a fourth embodiment of an electrophoresis device in accordance with the present invention.

FIG. 5 is a perspective view of a fourth embodiment of an electrophoresis device in accordance with the present invention. The electrophoresis device includes a first plate 170 and a second plate 172. The first plate 170 includes a substrate 174 patterned to define a plurality of channels, including channels 176, 178, 180, and 182. The second plate 172 is utilized to cover a face of the first plate 170 at which the plurality of channels are defined.

The first plate 170 and the second plate 172 can be formed of similar materials as the first plate 40 and the second plate 42 described with reference to FIG. 2. As with the embodiment of FIG. 2, the channels 176, 178, 180, and 182 can be formed during molding of the substrate 174 or can be etched or machined into the substrate 174.

A suitable gel is cast into the channels 176, 178, 180, and 182. The second plate 172 is secured over the first plate 170, either before or after casting the gel, to enclose the gel within the channels 176, 178, 180, and 182.

With or without the second plate 172 covering the first plate 170, samples of molecules are selectively applied to the channels 176, 178, 180, and 182. For example, with the second plate 172 removed from the first plate 170, the samples can be applied to the channels by a stamping process. As another example, the samples can be applied to the channels using wicks while the second plate 172 covers the first plate 170. Regardless of how the samples are applied, samples can be applied to all of the channels, or only to selected channels. Each channel can receive a different sample of molecules, or alternatively more than one channel can receive the same sample.

Once the samples are applied, the channels 176, 178, 180, and 182 provide a plurality of electrophoresis lanes. To selectively generate an electric field in each lane, a pair of electrodes is associated with each channel. With reference to the embodiment illustrated in FIG. 5, electrodes 190, 192, 194, and 196 are integrated with the substrate 174 at a terminal end of the channels 176, 178, 180, and 182, respectively. Electrodes 200, 202, 204, and 206 are integrated with the substrate 174 near a sample-receiving end of the channels 176, 178, 180, and 182, respectively. The electrodes 190, 192, 194, 196, 200, 202, 204, and 206 can be formed of a semiconductor material or a conductor material such as a metal or a polymer.

An electric field is generated in a channel by applying a voltage across its associated pair of electrodes. By including a respective pair of electrodes for each channel, the electric field in each channel can be independently controlled.

To sense molecular transport induced by the electric field, each channel can include a pair of sensing electrodes at a predetermined location as described with reference to the embodiment of FIG. 2. An impedance measurement can be performed using each pair of sensing electrodes to determine the presence of molecules from the sample at the predetermined location.

Alternatively, molecular transport can be sensed by a plurality of optical sensors, where at least one optical sensor is associated with each channel. The plurality of optical sensors can be integrated with either the first plate 170 or the second plate 172.

The first plate 170 optionally includes a heat sink 208 which functions in a manner similar to the heat sink 97. The heat sink 208 is located at an opposite face of the substrate 174 relative to the face at which the channels are defined.

Figure 6:
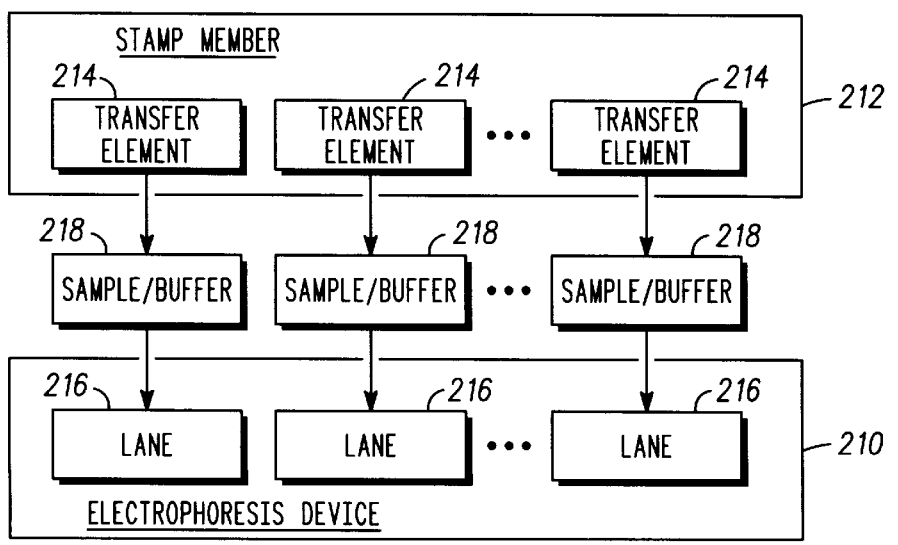
FIG. 6 is a perspective view that illustrates a second embodiment of an apparatus for applying samples to an electrophoresis device.

FIG. 6 illustrates a second embodiment of an apparatus for applying samples to an electrophoresis device 210. The apparatus includes a stamp member 212 which defines a plurality of transfer elements 214. The transfer elements 214 transfer to a plurality of electrophoresis lanes 216 samples and/or buffer solutions 218.

The transfer elements 214 are patterned according to locations of the electrophoresis lanes 216 on the electrophoresis device 210. Using the electrophoresis device illustrated in FIG. 5, for example, the transfer elements 214 can be patterned as a one-dimensional array and spaced in accordance with the spacing of the electrophoresis channels. Using the electrophoresis device illustrated in FIG. 2, for example, the transfer elements 214 can be patterned as a one-dimensional array and spaced in accordance with the spacing of the filling regions.

The transfer elements 214 can have any of a variety of forms. In one form, the transfer elements 214 include a plurality of reservoirs defined on a surface of the stamp member 212. Each reservoir has the form of a small inclusion in the stamp member 212 to hold a small quantity of the sample and/or the buffer solution 218. When the stamp member 212 is applied to a surface of the electrophoresis device 210, each sample and/or buffer solution 218 is deposited at its corresponding electrophoresis lane by a corresponding reservoir.

In a second form, the transfer elements 214 include a plurality of projected portions. The plurality of projected portions absorb the sample and/or the buffer solution 218 applied thereto. By contacting the stamp member 212 to the electrophoresis device 210, each sample and/or buffer solution 218 is transferred to its corresponding electrophoresis lane by a corresponding projected portion.

Various embodiments of stamp members and transfer elements, and methods of using same are described in the copending application "Methods and Systems for Biological Reagent Placement" which is incorporated by reference into the disclosure of the present application.

Figure 7:
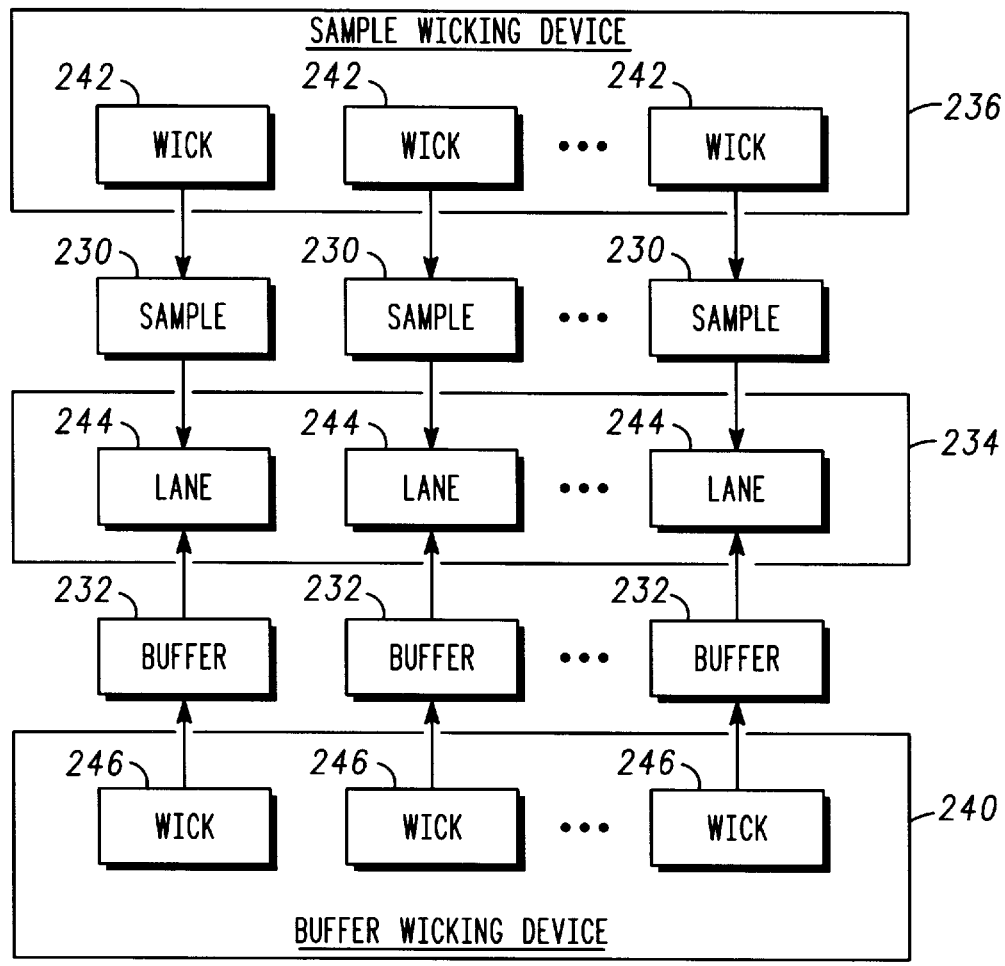
FIG. 7 is a general diagram that illustrates a third embodiment of an apparatus for applying samples and a buffer solution to an electrophoresis device.

FIG. 7 illustrates a third embodiment of an apparatus for applying samples 230 and a buffer solution 232 to an electrophoresis device 234. The apparatus includes a sample wicking device 236 and a buffer wicking device 240. The sample wicking device 236 includes a plurality of wicks 242. The wicks 242 are arranged to mate with a plurality of electrophoresis lanes 244 at a sample-receiving end of the electrophoresis device 234. The buffer wicking device 240 includes a plurality of wicks 246. The wicks 246 are arranged to mate with the electrophoresis lanes 244 at either the sample-receiving end or a terminal end of the electrophoresis device 234.

Using the electrophoresis device illustrated in FIG. 5, for example, the wicks 242 and the wicks 246 can be arranged in a one-dimensional array with adjacent wicks being spaced in accordance with the spacing of the electrophoresis channels. Using the electrophoresis device illustrated in FIG. 2, for example, the wicks 242 and the wicks 246 can be arranged in a one-dimensional array with adjacent wicks being spaced in accordance with the spacing of the filling regions.

The wicks 246 transfer the buffer solution 232 absorbed therein to the electrophoresis lanes 244. Thereafter, the buffer solution 232 diffuses to span the length of the electrophoresis lanes 244.

The wicks 242 transfer the samples 230 absorbed therein to the electrophoresis lanes 244. Each wick can be utilized to transfer a different sample to a different electrophoresis lane of the electrophoresis device, or can be utilized to transfer a common sample to a number of electrophoresis lanes.

Figure 8:
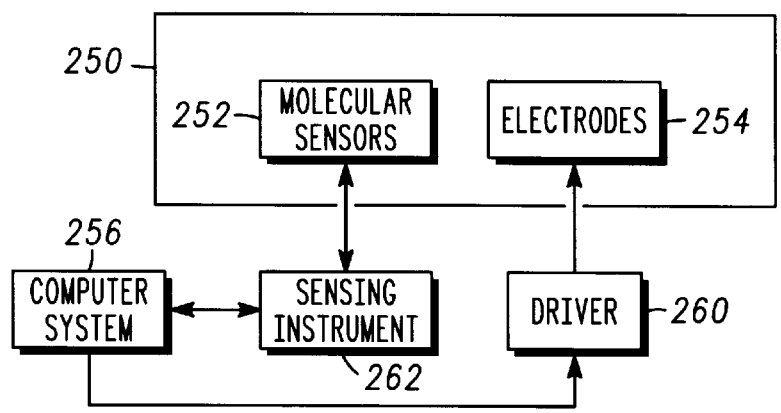
FIG. 8 is a general diagram that illustrates an embodiment of an electrophoresis system in accordance with the present invention.

FIG. 8 illustrates an embodiment of an electrophoresis system in accordance with the present invention. The electrophoresis system includes an electrophoresis device 250 having a plurality of electrophoresis lanes. Associated with the plurality of lanes are a plurality of molecular sensors 252 and a plurality of electrodes 254 for generating an electric field. Preferably, the electrophoresis device 250 is selected from the various embodiments of electrophoresis devices described herein.

The electrophoresis system further includes a computer system 256 or a like processing apparatus which commands various operations performed using the electrophoresis device 250. Typically, the computer system 256 includes: at least one input device such as a keyboard and/or a pointing device such as a mouse; a processor; a memory; at least one storage device such as a hard disk drive, a floppy disk drive, and/or an optical storage drive; and a display device such as a monitor. The operation of the computer system 256 is directed using computer-readable data stored by a computer-readable storage medium, such as a floppy disk, a hard disk, an optical disk, or the memory.

The computer system 256 commands a driver circuit 260 to selectively apply and remove a voltage to selected ones of the electrodes 254. The driver circuit 260 includes a plurality of electrophoresis drivers, each corresponding to one or more electrophoresis lanes, to provide power to produce predetermined electric field conditions in each of the electrophoresis lanes. Using this configuration, the electrophoresis process can be individually controlled in each of the electrophoresis lanes.

The computer system 256 commands a sensing instrument 262 to sense for the presence of sample molecules using the molecular sensors 252. In a preferred embodiment, each molecular sensor includes a pair of electrodes as described with reference to FIG. 2. Here, it is preferred that the sensing instrument 262 include an impedance meter to measure an impedance of the material between each pair of electrodes. The impedance meter can perform either an AC (alternating current) impedance measurement or a DC (direct current) impedance measurement.

Figure 9:
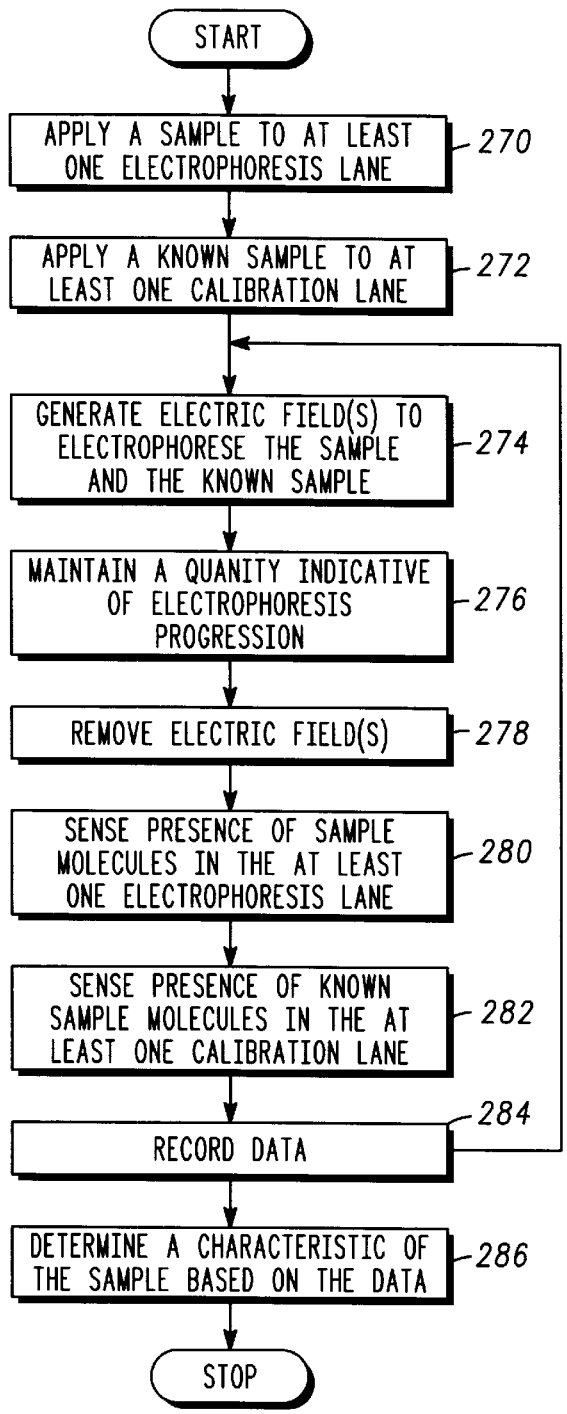
FIG. 9 is a flow chart of an embodiment of a method of electrophoresis in accordance with the present invention.

FIG. 9 is a flow chart of an embodiment of a method of electrophoresis in accordance with the present invention. Many of the steps of the method can be directed by the computer system 256 described with reference to FIG. 8. Although the method is described for electrophoresis of a single unknown sample using one or more electrophoresis lanes, it is noted that the method can be contemporaneously performed for each of a plurality of different unknown samples in a plurality of electrophoresis lanes.

As indicated by block 270, the method includes a step of applying a sample to at least one electrophoresis lane. Typically, the sample includes molecules having an unknown characteristic which is to be determined using the method.

The sample can be applied to the at least one electrophoresis lane using the apparatus described with reference to FIG. 4, FIG. 6, or FIG. 7. The sample can be applied to at least one electrophoresis channel which provides the at least one electrophoresis lane, or to a filling region associated with the at least one electrophoresis lane.

Preferably, the at least one electrophoresis lane includes a plurality of electrophoresis lanes. By applying the same sample to a plurality of electrophoresis lanes, a statistical analysis of results generated thereby can be performed.

As indicated by block 272, the method optionally includes a step of applying a known sample to at least one calibration lane. The known sample typically includes molecules having a known characteristic. In sequencing applications, the known sample can include a plurality of predetermined oligonucleotide fragments, or a plurality of oligonucleotide fragments having known lengths.

The known sample is applied to either at least one electrophoresis channel which provides the at least one calibration lane or to a filling region associated with the at least one calibration lane. The known sample can be applied to the at least one calibration lane using the apparatus described with reference to FIG. 4, FIG. 6, or FIG. 7.

Preferably, the at least one calibration lane includes a plurality of electrophoresis lanes. By applying the known sample to a plurality of electrophoresis lanes, a statistical analysis of results generated thereby can be performed.

It is noted that the sample and the known sample can be substantially simultaneously applied to their respective lanes, or can be sequentially applied to their respective lanes.

As indicated by block 274, the method includes a step of generating at least one electric field to electrophorese the sample, and optionally, to electrophorese the known sample. The at least one electric field can be substantially simultaneously applied to the at least one electrophoresis lane and to the at least one calibration lane, or can be sequentially applied to the at least one electrophoresis lane and the at least one calibration lane.

Using the system described with reference to FIG. 8, the step of generating the at least one electric field includes the computer system 256 communicating a signal to the driver 260. The signal indicates which lanes are to have an electric field generated therein. In response to receiving the signal, the driver 260 generates a predetermined voltage difference across predetermined pairs of the electrodes 254. In general, the driver 260 can provide either a continuous signal or a pulsed signal for each pair of the electrodes 254.

As indicated by block 276, the method includes a step of maintaining a quantity indicative of a progression of the electrophoresis. The quantity, herein referred to as a progression quantity, can indicate a time duration over which an electric field is applied to a lane. Alternatively, the progression quantity can indicate a count of pulses applied to an electrode pair by the driver 260. Generally, a respective progression quantity can be maintained for each lane. Each progression quantity can be maintained, e.g. can be determined and stored, using the computer system 256.

As indicated by block 278, the method includes an optional step of removing the electric field from the at least one electrophoresis lane, and optionally, the at least one calibration lane. The step of removing the electric field includes the computer system 256 communicating a signal to the driver 260. The signal indicates which lanes are to have its electric field removed. In response to receiving the signal, the driver 260 provides a voltage difference of zero across predetermined pairs of the electrodes 254.

As indicated by block 280, the method includes a step of sensing for a presence of sample molecules in the at least one electrophoresis lane. As indicated by block 282, the method optionally includes a step of sensing for a presence of known sample molecules in the at least one calibration lane.

The steps of sensing can be initiated by the computer system 256 communicating a request signal to the sensing instrument 262. The request signal indicates which selected ones of the molecular sensors 252 are to be utilized by the sensing instrument 262. In response to the request signal, the sensing instrument 262 can apply and/or receive a signal from each selected one of the molecular sensors 252. Based upon the applied signal and the received signal, the sensing instrument 262 forms a measurement quantity. The sensing instrument 262 communicates a signal representative of the measurement quantity to the computer system 256.

As Indicated by block 284, the method includes a step of recording data associated with the progression quantity and the results of the sensing steps. The data is recorded in a memory or a computer-readable storage medium associated with the computer system 256.

The data can include any one or more of: the measurement quantity, the progression quantity, a function of the measurement quantity, and a function of the progression quantity. For example, the data can include a data pair comprising the measurement quantity and the progression quantity. Alternatively, the data can include the progression quantity if the measurement quantity satisfies a predetermined condition. Various predetermined conditions of the measurement quantity are subsequently described with reference to FIG. 10.

Flow of the method can be directed to repeat the steps indicated by blocks 274, 276, 278, 280, 282, and 284 a number of times. As a result, a collection of data is produced and stored as the sample and the known sample migrate through the lanes. After forming the collection of data, flow of the method is directed to block 286.

Block 286 indicates a step of determining a characteristic of the sample based on the collection of data. Preferably, the characteristic is based upon either the mass of molecules in the sample, the size of molecules in the sample, or the length of molecule chains in the sample. Of particular interest is where the characteristic of the sample is based upon numbers of bases in DNA fragments or RNA fragments in the sample.

If the sample is electrophoresed in parallel by a plurality of electrophoresis lanes, and/or if the known sample is electrophoresed in parallel by a plurality of calibration lanes, the step of determining the characteristic can include a step of performing a statistical analysis of data generated thereby. The statistical analysis can include computing an estimate based on an estimator such as a mean, a trimmed mean, a median, and/or a maximum likelihood estimator for at least a subset of the data. Additionally, the statistical analysis can include computing a measure of variability of the subset of the data, such as a standard deviation or a variance. The measure of variability may be used to compute a confidence level for the estimate.

Figure 10:
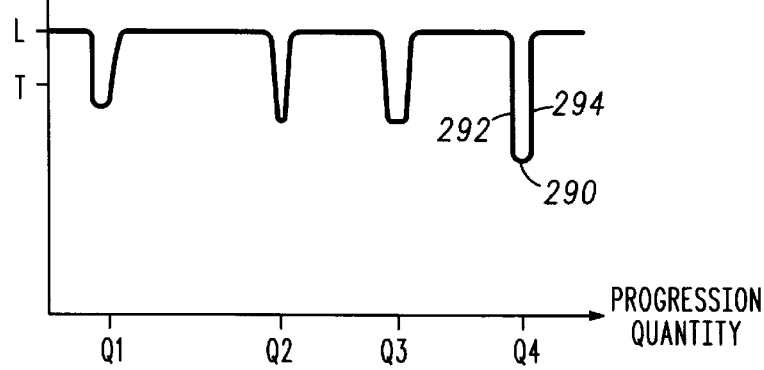
FIG. 10 illustrates an example plot of a measured quantity versus a progression quantity.

FIG. 10 illustrates an example plot of a measured quantity versus a progression quantity. The measured quantity, which can be an impedance, assumes a nominal level L when there is an absence of sample molecules proximate to a molecular sensor. As sample molecules electrophorese and become proximate to the molecular sensor, the measured quantity deviates from the nominal level. Thereafter, as the sample molecules depart from the molecular sensor, the measured quantity reverts to the nominal level.

The example plot is produced by four bands of molecules which cross the molecular sensor during electrophoresis. The four bands cross the molecular sensor at progression quantities of Q1, Q2, Q3, and Q4. The progression quantity at which the band crosses the molecular sensor can be defined by detecting any of the following conditions: (i) a crossing of the measurement quantity beyond a threshold T; (ii) a local extremum point 290; (iii) a difference between the measurement quantity and a previous value of the measurement quantity; or (iv) a rate of change of the measurement quantity. The condition can be based on either the local extremum point 290, a leading edge 292, or a trailing edge 294 of the plot of the measurement quantity. Regardless of how the progression quantities Q1, Q2, Q3, and Q4 are defined, the data recorded in the step indicated by block 284 preferably includes the values of Q1, Q2, Q3, and Q4. In this manner, a progression quality, such as a time interval for a molecule to be transported to a fixed sensor, is measured. The progression quantity, such as the time interval, can be mapped to a physical property of the molecule, such as the molecular size.

Figure 11:
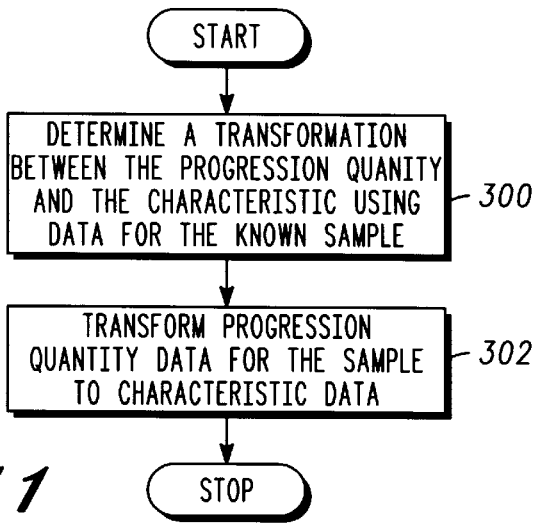
FIG. 11 is a flow chart of an embodiment of a method of determining a characteristic of the sample based on a collection of data.

FIG. 11 is a flow chart of an embodiment of a method of determining a characteristic of the sample based on a collection of data. Various characteristics, including size, mass, or length of molecules in the sample can be determined. For the purpose of illustration, the method is described for the characteristic being a size (i.e. a length or a number of nucleotide bases) of DNA fragments or RNA fragments within the sample.

As indicated by block 300, the method includes a step of determining a transformation between the progression quantity and the characteristic using data for the known sample. Assuming the plot of FIG. 10 is generated from electrophoresis of the known sample, the data for the known sample includes the values of Q1, Q2, Q3 and Q4, and known sizes S1, S2, S3, and S4 (in increasing order) of the fragments. The transformation can include a linear or a nonlinear curve fit between the known sizes and the progression quantities.

As indicated by block 302, the method includes a step of transforming progression quantity data associated with the sample to form characteristic data. The progression quantity data is transformed using the transformation determined in the previous step.

Figure 12:
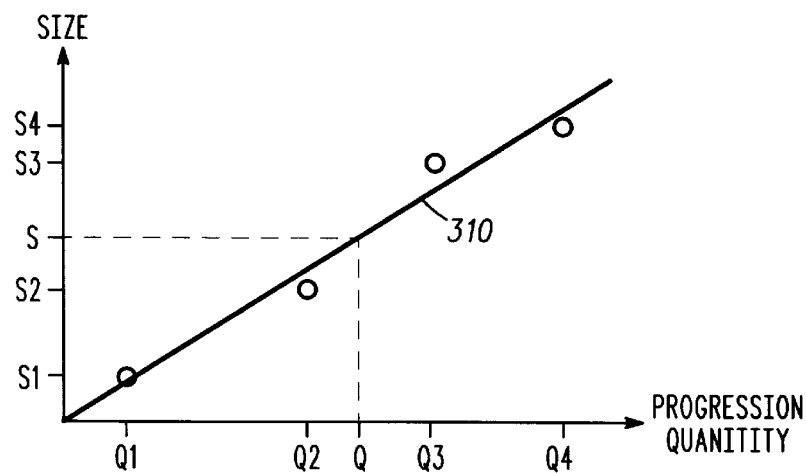
FIG. 12 illustrates an example of a linear transformation for determining sizes of molecules in the sample.

FIG. 12 illustrates an example of a linear transformation for determining sizes of molecules in the sample. The linear transformation is provided by a line 310 fit to a collection of data including the data pairs (Q1, S1), (Q2, S2), (Q3, S3), and (Q4, S4). The linear transformation can be computed using a line fitting routine such as least squares regression. Using the linear transformation, a band of molecules in the sample detected at a progression quantity value of Q transforms to a size of S.

Figure 13:
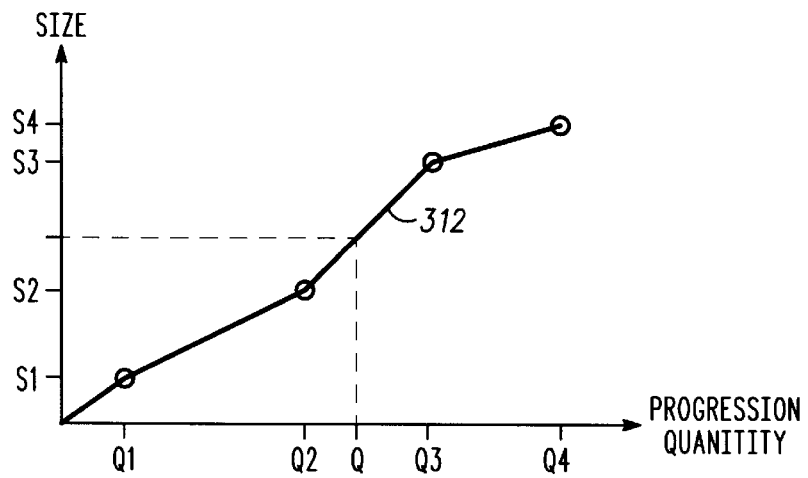
FIG. 13 illustrates an example of a second transformation for determining sizes of molecules in the sample.

FIG. 13 illustrates an example of a second transformation for determining sizes of molecules in the sample. The second transformation is provided by a piecewise-linear curve 312 fit to the collection of data of (Q1, S1), (Q2, S2), (Q3, S3), and (Q4, S4). Using the second transformation, a band of molecules in the sample detected at a progression quantity value of Q transforms to a size of S. In this example, the size S is determined by interpolating between (Q2, S2) and (Q3, S3).

Figure 14:
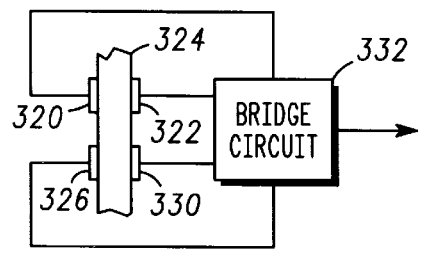
FIG. 14 is a general diagram that illustrates an embodiment of an apparatus for sensing sample molecules for use in embodiments of the electrophoresis device.

FIG. 14 illustrates an embodiment of an apparatus for sensing sample molecules for use in embodiments of the electrophoresis device. The apparatus includes a first molecular sensor comprising a first electrode 320 and a second electrode 322 on opposite sides of an electrophoresis channel 324. The molecular sensor further includes a second molecular sensor comprising a third electrode 326 and a fourth electrode 330 on opposite sides of the electrophoresis channel 324. As with the sensing electrodes described with reference to FIG. 2, the electrodes 320, 322, 326, and 330 can be formed of a conductor or a semiconductor material, and can abut or be insulated from an interior of the electrophoresis channel 324.

The apparatus further includes a circuit, such as a bridge circuit 332, which produces a signal based upon a difference between a parameter sensed by the first molecular sensor and a parameter sensed by the second molecular sensor. Preferably, the bridge circuit 332 produces a signal based upon a difference between an impedance sensed by the first molecular sensor and an impedance sensed by the second molecular sensor. The bridge circuit 332 can include a Wheatstone bridge, for example, to produce a signal based upon the impedance difference. The bridge circuit 332 can apply either an AC signal or a DC signal to the electrodes 320, 322, 326, and 330 to detect the impedance difference.

The above-described apparatus is advantageous in sensing sample molecules in the electrophoresis channel 324 based upon a spatial, differential impedance measurement rather than an absolute impedance measurement. Consequently, the sample molecules can be detected with less dependence on the absolute impedance of a gel in the electrophoresis channel 324.

Figure 15:
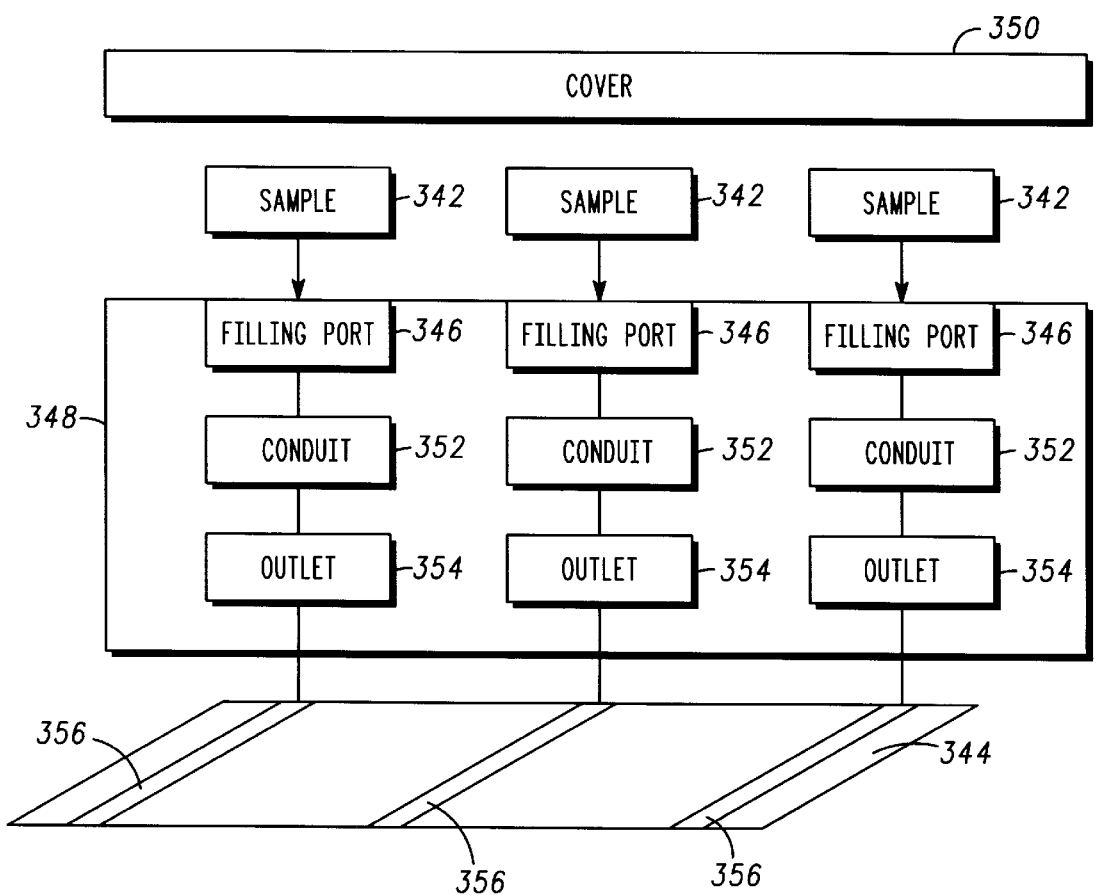
FIG. 15 is a block diagram of an embodiment of an apparatus for applying a plurality of samples to an electrophoresis device.

FIG. 15 is a block diagram of an embodiment of an apparatus 340 for applying a plurality of samples 342 to an electrophoresis device 344. The apparatus 340 defines a plurality of filling ports 346. Each of the filling ports 346 receives a respective one of the samples 342. If desired, each of the filling ports 346 can receive a different sample.

Preferably, the filling ports 346 are all accessible for receiving the samples 342 at a face 348 of the apparatus 340. When the apparatus 340 s oriented to receive the samples 342, the face 348 can be a top face of the apparatus 340.

Once the samples 342 have been dispensed into the filling ports 346, a cover 350 is applied to the face 348. The cover 350 seals the samples 342 within the apparatus 340, and preferably, seals the samples 342 within the filling ports 346. Preferably, the cover 350 is formed of a deformable material such as a flexible plastic, an elastomer, or rubber. As a result, a pressure applied to the filling ports 346 can he varied by depressing the cover 350.

After applying the cover 350 to the face 348, the samples 342 contained in the apparatus 340 can be dispensed into the electrophoresis device 344 in a manner described hereinafter, or can be stored for subsequent dispensing. Although the apparatus 340 generally can be stored in any orientation when containing the samples 342, in some instances it may be desired to maintain the orientation of the apparatus 340 so that the face 348 is the top face.

The apparatus 340 further includes a plurality of conduits 352 and a plurality of outlets 354. Each of the conduits 352 provides a fluidic communication path between a respective one of the filling ports 346 and a respective one of the outlets 354. As a result, the conduits 352 provide a plurality of fluidic communication paths to direct the samples 342 from the filling ports 346 to the outlets 354. The samples 342 are forced through the conduits 352 by an application of pressure to the filling ports 346. The pressurization of the filling ports 346 can be accomplished by depressing the cover 350.

The outlets 354 are arranged to align with filling regions and/or electrophoresis lanes 356 defined by the electrophoresis device 344. Typically, the outlets 354 are arranged in a one-dimensional pattern. It desired, each of the outlets 354 can be shaped as a gasket as described with reference to FIG. 4.

During dispensing, the electrophoresis device 344 can be oriented so that the electrophoresis lanes 356 are substantially parallel to the plane of the face 348, as illustrated. Alternatively, the electrophoresis device 344 can be oriented so that the electrophoresis lanes 356 are transverse to the plane of the face 348.

For ease in applying the samples 342 to the apparatus 340, it is preferred that the width of each of the filling ports 348 be greater than the width of each of the outlets 354. Further, it is preferred that the filling ports 348 be arranged to have a greater pitch than the outlets 354. To accomplish these preferred specifications, the filling ports 346 are arranged in a two-dimensional pattern, such as a two-dimensional array, at the face 348. The two-dimensional pattern can be configured in accordance with a predetermined microplate standard, such as standards for 12-well microplates, 40-well microplates, 96-well microplates, 384-well microplates, and 1728-well microplates, for example.

Figure 16:
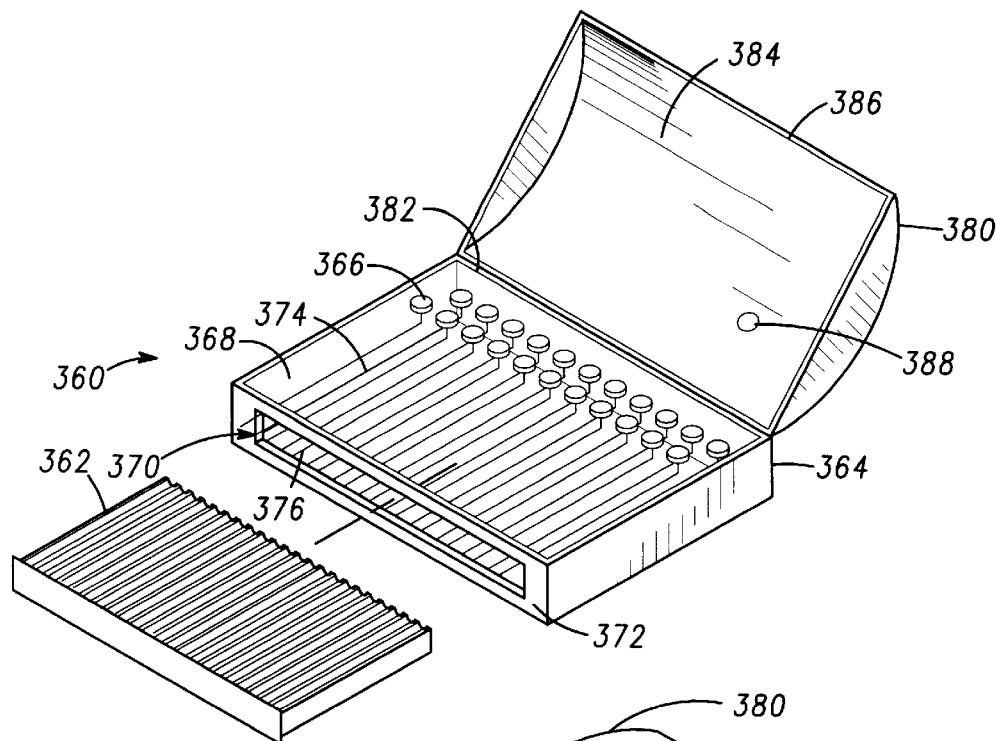
FIG. 16 is a perspective view of another embodiment of an apparatus for applying a plurality of samples to an electrophoresis device.

FIG. 16 is an illustration of another embodiment of an apparatus 360 for applying a plurality of samples to an electrophoresis device 362. The apparatus 360 comprises a body 364 which defines a plurality of filling ports. A representative one of the filling ports is indicated by reference numeral 366. The filling ports 366 are arranged as a two-dimensional array at a top face 368 of the body 364.

The body 364 further defines a slot 370 sized to receive at least a portion of the electrophoresis device 362. An opening to the slot 370 is located at a second face 372 of the body 364. Preferably, the second face 372 is oriented transverse to the top face 368 to provide an elbow-type filling apparatus.

The body 364 can be formed of one or more materials, including but not limited to, plastic, polystyrene, polypropylene, and Nylon. Preferably, the body 364 is rigid or semi-rigid.

The apparatus 360 includes a plurality of conduits, a representative one indicated by reference numeral 374, in fluidic communication with the filling ports 366. The conduits 374 have the form of tubes which define a plurality of outlets, a representative one indicated by reference numeral 376, at their terminal ends. The outlets 376 are positioned to be accessible within the slot 370.

Each of the outlets 376 can be sized to fit within a filling region and/or electrophoresis lane of the electrophoresis device 362. Alternatively, each of the outlets 376 can be shaped and sized as a gasket described with reference to FIG. 4.

Preferably, each of the filling ports 366 has a volume which is greater than an interior volume of a respective one of the conduits 374 coupled thereto. More preferably, each of the filling ports 366 has a volume greater than or equal to the sum of the interior volume of the conduit and the volume of the filling region of the electrophoresis device 362. Generally, each of the filling ports 366 has a volume greater than or equal to the sum of the interior volume of the conduit and a volume which is to be dispensed.

The apparatus 360 further includes a cover 380 which selectively covers and uncovers the top face 368 of the body 364. To facilitate covering and uncovering of the top face 368, the cover 380 is pivotably-connected to the body 364 along an edge 382 using a hinge or the like. The cover 380 is placed in an uncovered state, as illustrated, for dispensing the samples into the filling ports 366. In a covered state, the cover 380 seals the samples within the apparatus 360 for storage and for dispensing to the electrophoresis device 362.

The cover 380 includes an interior portion 384 having a concave shape, and an edge portion 386 shaped to contact the top face 368 in the covered state. In general, the interior portion 384 can have other concave shapes than that illustrated. Here, for example, the interior portion 384 can be dome-shaped.

Preferably, the cover 380 is formed of a deformable material such as a flexible plastic, an elastomer, or rubber. The interior portion 384 and the edge portion 386 can be formed of the same deformable material, if desired. Alternatively, the edge portion 386 can be formed of a different material than the interior portion 384.

The cover 380 defines an opening 388 which provides a fluidic communication path between a first side and a second side. The opening 388 equalizes the pressure of a first environment adjacent the first side and a second environment adjacent the second side of the cover 380. A pressure difference between the first environment and the second environment can be formed by covering the opening 388.

Figure 17:
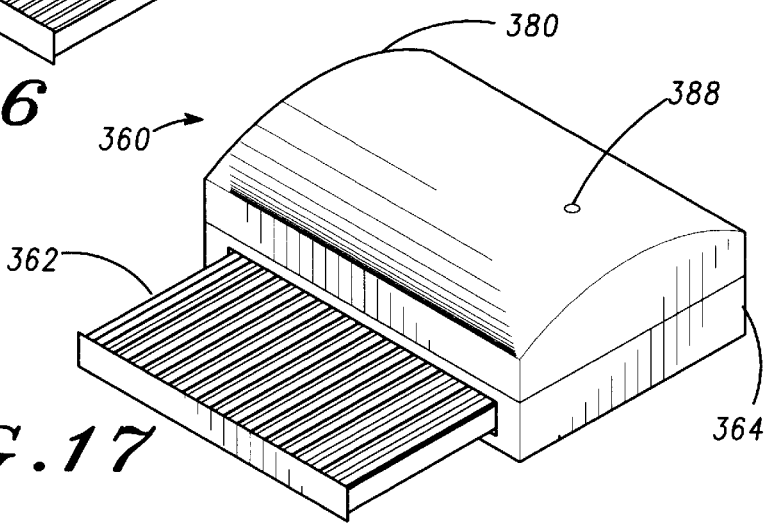
FIG. 17 is an illustration of the embodiment of the apparatus of FIG. 16 in a covered state.

FIG. 17 is an illustration of the embodiment of the apparatus 360 of FIG. 16 in a covered state. Here, the cover 380 is placed over the top face 368. In the covered state, the edge portion 386 contacts the periphery of the top face 368 to provide a seal.

The electrophoresis device 362 is shown inserted into the slot 370. When inserted, the filling regions of the electrophoresis device 362 mate with the outlets 376 of the apparatus 360.

The samples within the filling ports 366 are dispensed to the electrophoresis device 362 by covering the opening 388, and applying a force to the cover 380. The cover 380 deforms in response to applying the force, which in turn increases a pressure on the samples in the filling ports 366. The increase in pressure acts to force the samples through the conduits 374, toward the outlets 376, and into the filling regions of the electrophoresis device 362. Once the filling regions are filled, the force to the cover 380 can be removed. Further, if an elastomeric material is used to form the cover 380, the opening 388 can be uncovered to restore the cover 380 to its original form.

The electrophoresis device 362 can be removed from the apparatus 360 after the samples are applied thereto. Thereafter, the apparatus 360 can be stored for subsequent dispensing of samples in the same electrophoresis device 362 or another like electrophoresis device. After dispensing the samples one or more times, the apparatus 360 can be cleaned and reused, or can be disposed.

Figure 18:
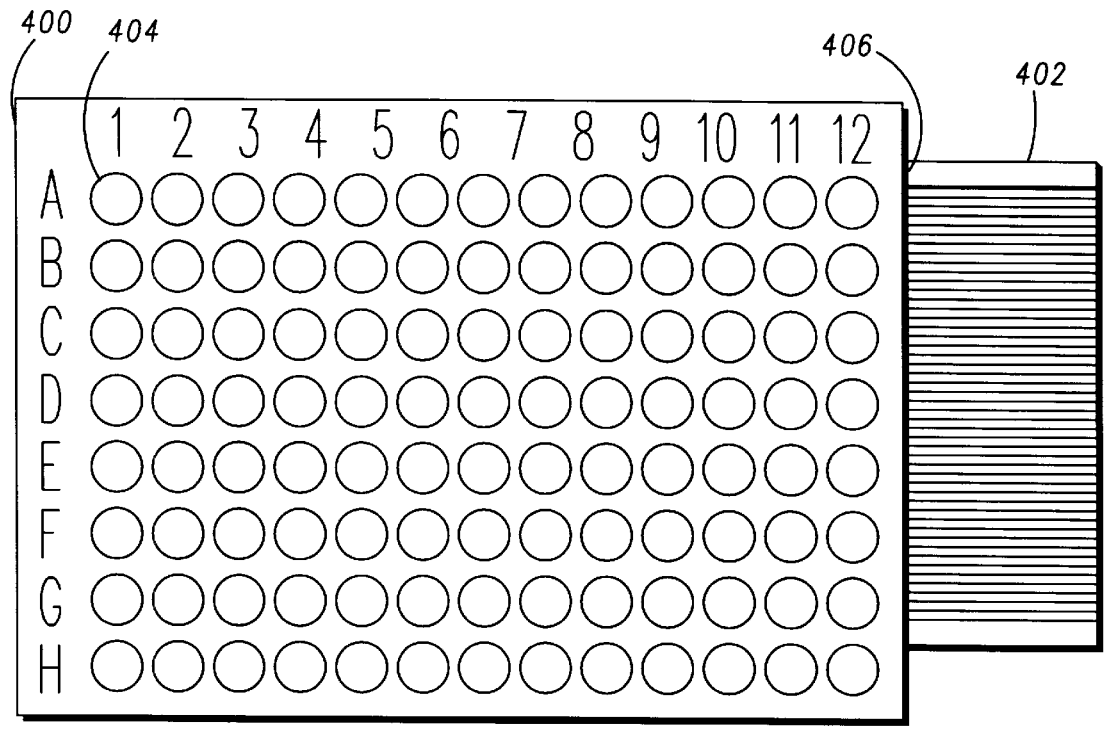
FIG. 18 is a top view of a third embodiment of an apparatus for dispensing a plurality of samples to an electrophoresis device.

FIG. 18 is a top view of a third embodiment of an apparatus 400 for dispensing a plurality of samples to an electrophoresis device 402. The apparatus 400 includes a plurality of filling ports, a representative one being indicated by reference numeral 404, which are arranged in accordance with a predetermined microplate standard. As illustrated, the filling ports can be arranged in accordance with a 96-well microplate standard, for example.

The apparatus 400 includes a plurality of conduits (not specifically illustrated) and a plurality of outlets (not specifically illustrated) to communicate samples from the filling ports to the electrophoresis device 402. The electrophoresis device 402 includes at least 96 filling regions and/or at least 96 electrophoresis lanes to receive the samples.

To receive the samples, the electrophoresis device 402 is inserted into a side slot 406 of the apparatus 400. The apparatus 400 can include a cover (not specifically illustrated) as described earlier to pump the samples into the electrophoresis device 402.

Although illustrated for dispensing samples in an electrophoresis device, it is noted that the apparatus described with reference to FIGS. 15–18 can be used to dispense samples in any assay member. Here, the slot 370 and the side slot 406 can be generally referred to as assay-member-receiving slots which are shaped and sized to receive an assay member.

The assay-member-receiving slot can be sized to simultaneously receive a plurality of assay members. The plurality of assay members can be stacked one above another within the assay-member-receiving slot. A plurality of electrophoresis devices as described herein can be stacked for placement within the slot 370 or the side slot 406. The apparatus 360 can include a second plurality of outlets in fluidic communication with the filling ports 366 to dispense samples to a second one of the electrophoresis devices. The second plurality of outlets are arranged in a one-dimensional pattern substantially parallel to the one-dimensional pattern of the outlets 376. The second plurality of outlets can be located above or below the outlets 376, for example. Other pluralities of outlets can be included based upon the number of electrophoresis devices which are to be filled concurrently.

It is further noted that the apparatus described with reference to FIGS. 15–18 can dispense other substances, such as gels and buffers, to an assay member.

Figure 19:
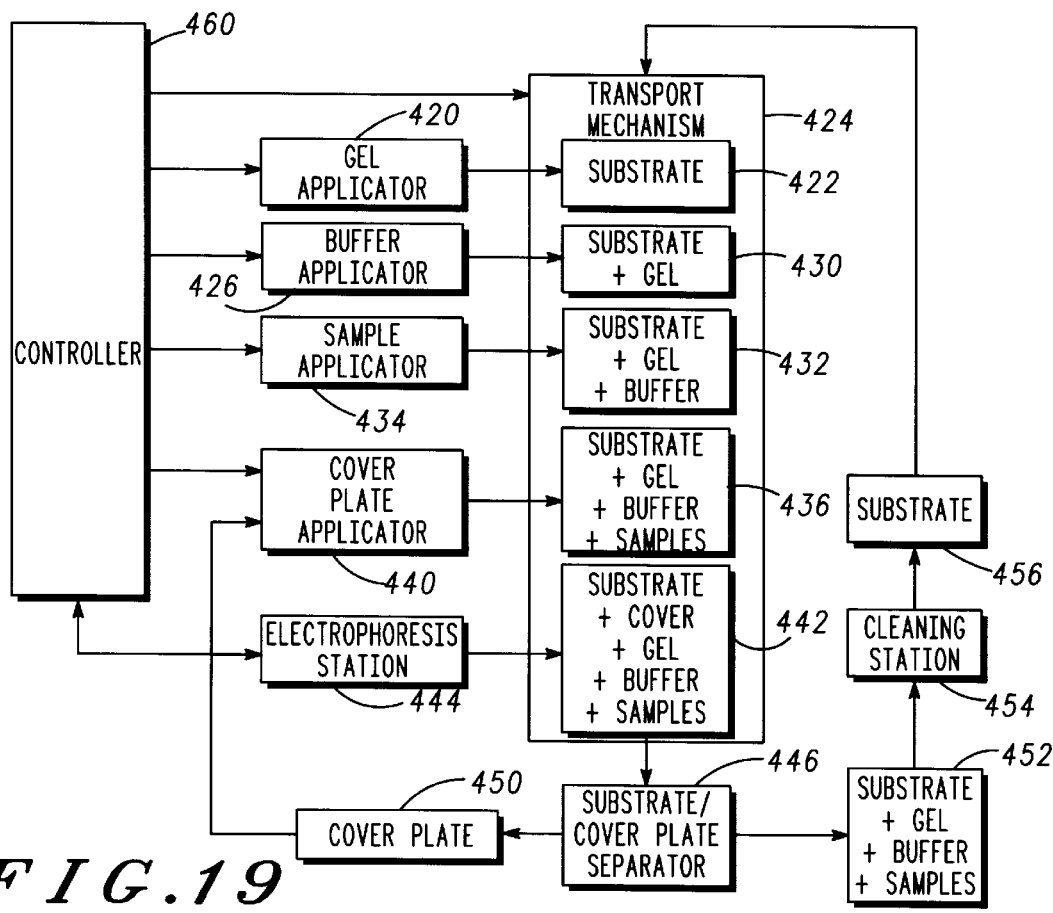
FIG. 19 is a block diagram of an embodiment of an automated electrophoresis system in accordance with the present invention.

FIG. 19 is a block diagram of an embodiment of an automated electrophoresis system in accordance with the present invention. The automated electrophoresis system includes a gel applicator 420 which applies a gel to a substrate 422. Preferably, the substrate 422 is provided by an embodiment of an electrophoresis device described herein. For example, the substrate 422 can be provided by the electrophoresis device described with reference to FIG. 1, the first plate 40 described with reference to FIG. 2, or the first plate 170 described with reference to FIG. 5. The gel applicator 420 can include a dispenser to dispense the gel to a plurality of channels defined by the substrate 422, and a blade to distribute the gel along the plurality of channels. Alternatively, the gel applicator 420 can include a plurality of transfer elements arranged to stamp lanes of the gel onto the substrate 422. Here, the substrate 422 can include a substantially flat surface onto which a plurality of electrophoresis lanes is stamped.

The automated electrophoresis system further includes a transport mechanism 424 to transport substrates from the gel applicator 420 to a buffer applicator 426. The transport mechanism 424 can include a linear conveyor, a rotary conveyor, or a robotic arm, for example, to transport the substrates.

As illustrated, the buffer applicator 426 applies a buffer solution to a substrate 430 having lanes of gel. Preferably, the buffer applicator 426 includes an embodiment of the stamp member 212 described with reference to FIG. 6, or an embodiment of the buffer wicking device 240 described with reference to FIG. 7.

The transport mechanism 424 transports a substrate 432 having the gel and the buffer solution to a sample applicator 434. The sample applicator 434 applies a plurality of samples to electrophoresis lanes supported by the substrate 432. Preferably, the sample applicator 434 includes an embodiment of an apparatus for applying samples to an electrophoresis device described with reference to FIG. 4, FIG. 6, or FIG. 7.

A substrate 436 having the gel, the buffer solution, and the samples is transported by the transport mechanism 424 to a cover plate applicator 440. The cover plate applicator 440 applies a cover plate to the substrate 436 to cover a face of the substrate 436 exposing the gel, the buffer solution, and the samples. Examples of the cover plate include the second plate 42 described with reference to FIG. 2 and the second plate 172 described with reference to FIG. 5.

The cover plate applicator 440 can include a robotic arm or the like to apply the cover plate to the substrate 436. Alternatively, the cover plate applicator 440 can direct the substrate 436 utilizing a robotic arm or the like to contact the cover plate.

The transport mechanism 424 transports a substrate 442 having the gel, the buffer solution, the samples, and the cover plate to an electrophoresis station 444. The electrophoresis station 444 electrophoreses the samples supported by the substrate 442. Preferably, the electrophoresis station 444 includes an embodiment of an electrophoresis system described with reference to FIG. 8 and uses an embodiment of a method of electrophoresis described with reference to FIG. 9. The electrophoresis station 444 can further perform a step of linking the electrophoresis system to electrodes and molecular sensors of the substrate 442. The electrophoresis station 444 can be linked to the electrode and the molecular sensors via a wireline connection or via a wireless connection.

After electrophoresing the samples, the transport mechanism 424 transports the substrate 442 to a separator 446. The separator 446 separates a cover plate 450 from a substrate 452 having the gel, the buffer solution, and the samples. The separator 446 can include a robotic arm or the like to perform the separation.

The cover plate 450 is directed back to the cover plate applicator 440 for subsequent application to a substrate. The substrate 452 is directed to a cleaning station 454 to remove the gel, the buffer, and the samples therefrom. A clean substrate 456 having the gel, the buffer, and the samples removed therefrom by the cleaning station 454 is directed to the transport mechanism 424 for subsequent use.

A controller 460 directs the operation of the transport mechanism 424, the gel applicator 420, the buffer applicator 426, the sample applicator 434, the cover plate applicator 440, and the electrophoresis station 444. The controller 460 orchestrates the actions of the above-identified components to concurrently process a plurality of substrates, such as the substrates 422, 430, 432, 436, 442, 452, and 456, in an assembly-line manner. The controller 460 can include a computer system, such as the computer system 256 described with reference to FIG. 8, which produces control signals to control each of the above-identified components.

The automated electrophoresis system can be utilized for applications such as sequencing and fragment sizing. In a sequencing application, a sample is prepared for performing a restriction analysis. In particular, one or more restriction enzymes are applied to the sample to form a plurality of fragment samples. The fragment samples are applied to at least one substrate by the sample applicator 434. If the number of fragment samples is greater than a number of electrophoresis lanes supported by a single substrate, the sample applicator 434 distributes the fragment samples to a plurality of substrates. The controller 460 compiles results obtained by the electrophoresis station 444 for one or more substrates to determine a characteristic of the sample, e.g. a base sequence for the sample. The controller 460 provides a digital representation of the characteristic which can be stored and/or displayed.

Figure 20:
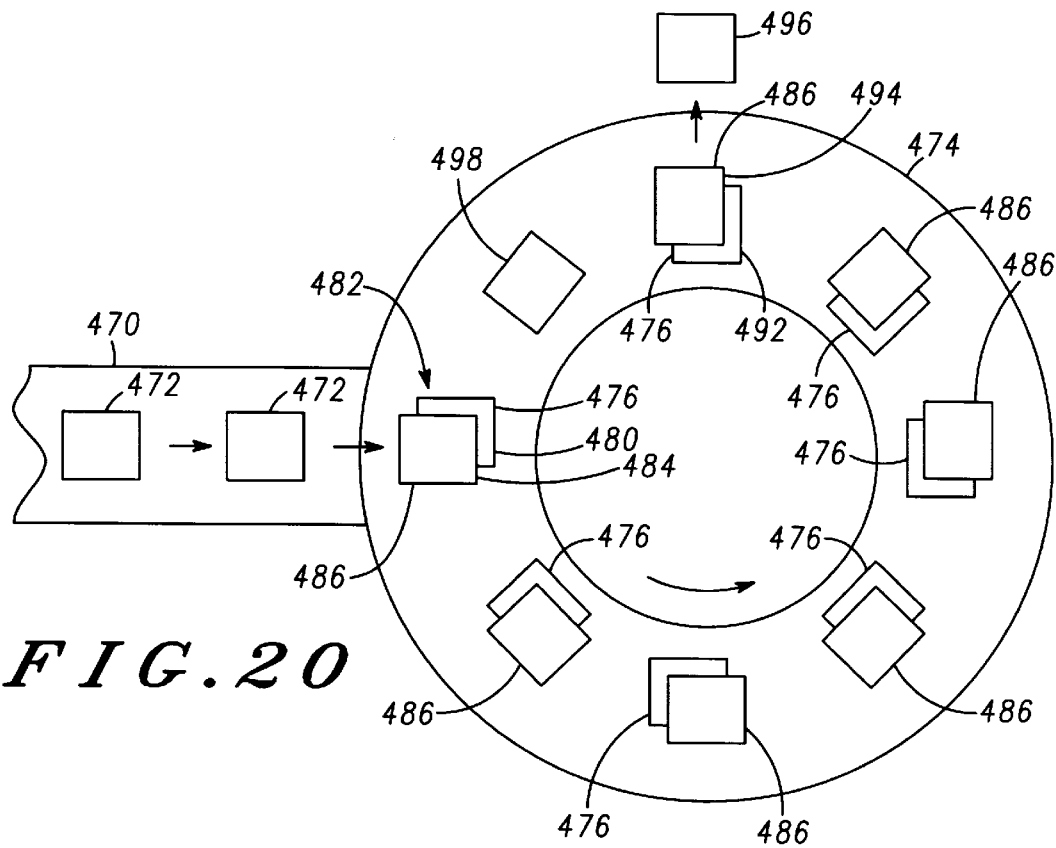
FIG. 20 is a diagram that illustrates an embodiment of a transport mechanism in accordance with the present invention.

FIG. 20 illustrates an embodiment of a transport mechanism in accordance with the present intention. The transport mechanism includes a first conveyor 470 which transports substrates between at least two stations, namely a first station and a second station, of an automated electrophoresis system. Examples of the first station and the second station include, but are not limited to, the gel applicator 420, the buffer applicator 426, the sample applicator 434, and the cover plate applicator 440 described with reference to FIG. 19. In general, the first conveyor 470 can transport substrates to/from each of the above-listed applicators.

As illustrated, the first conveyor 470 can have the form of a linear conveyor which either contemporaneously or simultaneously transports a plurality of substrates 472 through the automated electrophoresis system. With reference to FIG. 19, the first conveyor 470 can transport the substrate 422 to the gel applicator 422, the substrate 430 to the buffer applicator 426, the substrate 432 to the sample applicator 434, and the substrate 436 to the cover plate applicator 440 either contemporaneously or simultaneously.

The transport mechanism further includes a second conveyor 474 which either contemporaneously or simultaneously transports a plurality of substrates 476 from the second station to a third station. The second station can include any of the above-listed applicators. Preferably, the third station includes the separator 446 described with reference to FIG. 19.

As illustrated, the second conveyor 474 can have the form of a rotary conveyor, such as a carousel, which receives a substrate 480 from the first conveyor 470 at a first position 482. A cover plate 484 is applied to the substrate 480 at the first position 482. The plurality of substrates 476 and a plurality of cover plates 486 associated therewith are transported from the first position 482 to a second position 490.

An electrophoresis station, such as the electrophoresis station 444, electrophoreses samples supported by at least one of the substrates 476 between the first position 482 and the second position 490. The electrophoresis station can perform steps of electrophoresis and sensing/detection as the second conveyor 474 transports the plurality of substrates 476. Preferably, the electrophoresis station simultaneously electrophoreses samples supported by at least two of the plurality of substrates 476 being transported by the second conveyor 474.

At the second position 490, a substrate 492 is separated from its cover plate 494. A separated substrate 496 can be directed to a cleaning station, such as the cleaning station 454, for re-use. A separated cover plate 498 is transported back to the first position 482 by the second conveyor 474 for re-use.

Figure 21:
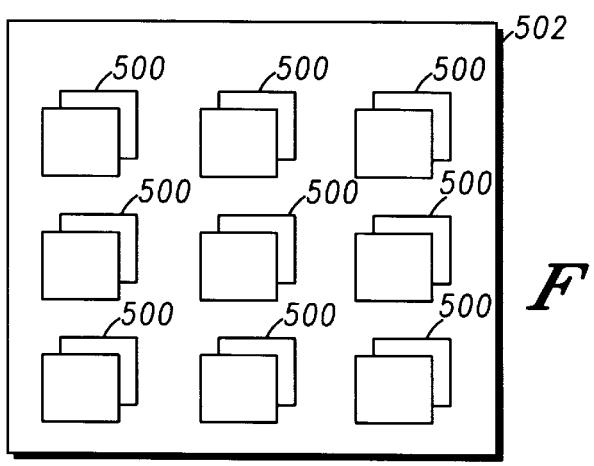
FIG. 21 illustrates another approach to contemporaneously electrophoresing samples supported by a plurality of electrophoresis devices.

FIG. 21 illustrates another approach to contemporaneously electrophoresing samples supported by a plurality of electrophoresis devices. In this approach, a plurality of electrophoresis devices 500 are placed on a carrier 502. The carrier 502 can have a form of a tray or the like having a substantially planar portion to support the electrophoresis devices 500.

The samples can be applied to the electrophoresis devices 500 prior to being placed on the carrier 502. Alternatively, the samples can be applied while the electrophoresis devices 500 are supported by the carrier 502. The samples are either contemporaneously or simultaneously electrophoresed while the electrophoresis devices 500 are supported by the carrier 502. Preferably, steps of sensing and/or detection are performed during electrophoresis while the electrophoresis devices 500 are supported by the carrier 502.

Figure 22:
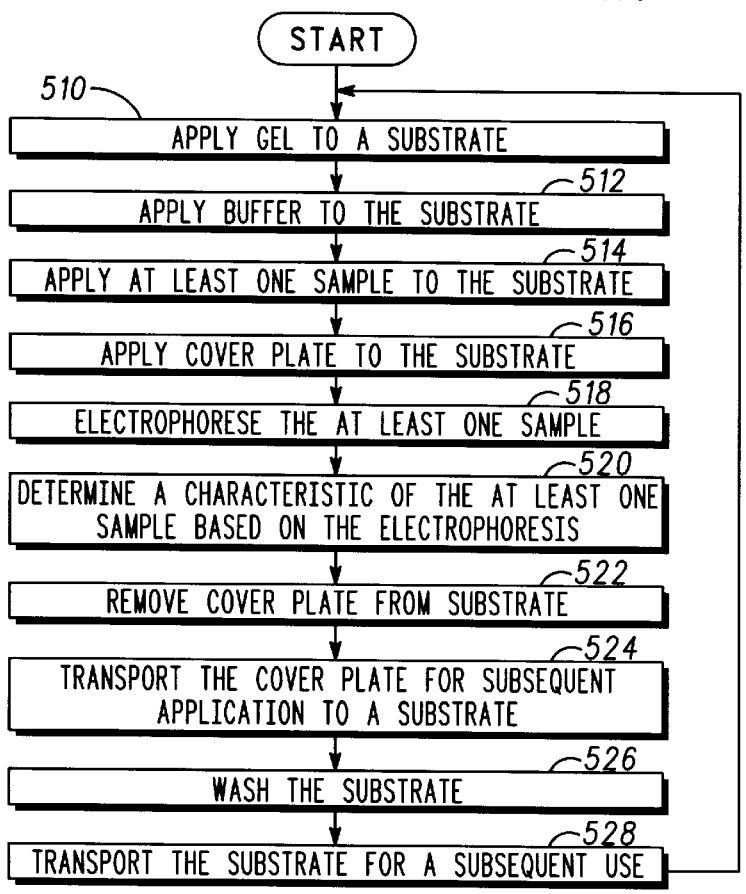
FIG. 22 is a flow chart of an embodiment of a method of electrophoresis for a single electrophoresis device.

FIG. 22 is a flow chart of an embodiment of a method of electrophoresis for a single electrophoresis device. Preferably, the method is performed using the automated electrophoresis system described with reference to either FIG. 19 or FIG. 23.

As indicated by block 510, the method includes a step of applying a gel to a substrate of the electrophoresis device. The gel can be applied using the gel applicator 420. A step of transporting the substrate to the gel applicator 420 or transporting the gel applicator 420 to the substrate can be performed prior to applying the gel.

As indicated by block 512, the method further includes a step of applying a buffer to the substrate. The buffer can be applied using the buffer applicator 426. A step of transporting the substrate to the buffer applicator 426 or transporting the buffer applicator 426 to the substrate can be performed prior to applying the buffer.

As indicated by block 514, the method includes a step of applying at least one sample to the substrate. The at least one sample can be applied using the sample applicator 434. A step of transporting the substrate to the sample applicator 434 or transporting the sample applicator 434 to the substrate can be performed prior to applying the at least one sample. It is noted that the at least one sample can include at least one known sample which is applied for calibration purposes as described herein.

As indicated by block 516, the method includes a step of applying a cover plate to the substrate. The cover plate can be applied using the cover plate applicator 440. A step of transporting the substrate to the cover plate applicator 440 or transporting the cover plate applicator 440 to the substrate can be performed prior to applying the cover plate.

As indicated by block 518, the method includes a step of electrophoresing at least one sample supported by the substrate. The step of electrophoresing can be performed using the electrophoresis station 444. A step of transporting the substrate to the electrophoresis station 444 or transporting the electrophoresis station 444 to the substrate can be performed prior to performing the step of electrophoresis.

Preferably, the step of electrophoresing the at least one sample includes a step of sensing a migration of the at least one sample using at least one molecular sensor associated with either the substrate 442 or the cover plate. Further, either the substrate 442 or the cover plate can include a transmitter for wirelessly transmitting a signal derived from the at least one molecular sensor. For example, the transmitter can be included in a radio frequency tag or a transponder integrated with either the substrate 442 or the cover plate.

To wirelessly receive the signal from the transmitter, the electrophoresis station can include a wireless receiver. For example, the receiver can be included in a radio frequency tag communicating device to communicate with a radio frequency tag integrated with either the substrate 442 or the cover plate. The tag communicating device can be utilized to poll a plurality of radio frequency tags associated with a plurality of electrophoresis devices.

As indicated by block 520, the method includes a step of determining a characteristic of the at least one sample based on the electrophoresis. The characteristic is determined based upon data generated using the at least one molecular sensor associated with the substrate 442 and/or the cover plate. The characteristic can be determined using the electrophoresis station 444 and/or the controller 460.

As indicated by block 522, the method includes a step of removing the cover plate from the substrate. The cover plate can be removed using the separator 446. A step of transporting the substrate to the separator 446 or transporting the separator 446 to the substrate can be performed prior to removing the cover plate.

As indicated by block 524, the method includes a step of transporting the cover plate for subsequent application to a substrate. This step can include transporting the cover plate to the cover plate applicator 440.

As indicated by block 526, the method includes a step of washing the substrate. The substrate can be washed by the cleaning station 454 to remove the gel, the buffer, and the electrophoresed samples.

As indicated by block 528, the method includes a step of transporting the substrate for a subsequent use. Thereafter, flow of the method is directed back to the step indicated by block 510 so that a subsequent sample can be electrophoresed using the substrate.

It is noted that the above-listed steps can be performed in a different order than that illustrated in FIG. 22. For example, the cover plate can be applied to the substrate prior to applying the at least one sample. Further, some of the above-listed steps can be performed concurrently. For example, the steps of transporting the cover plate and transporting the substrate can be performed concurrently.

Figure 23:
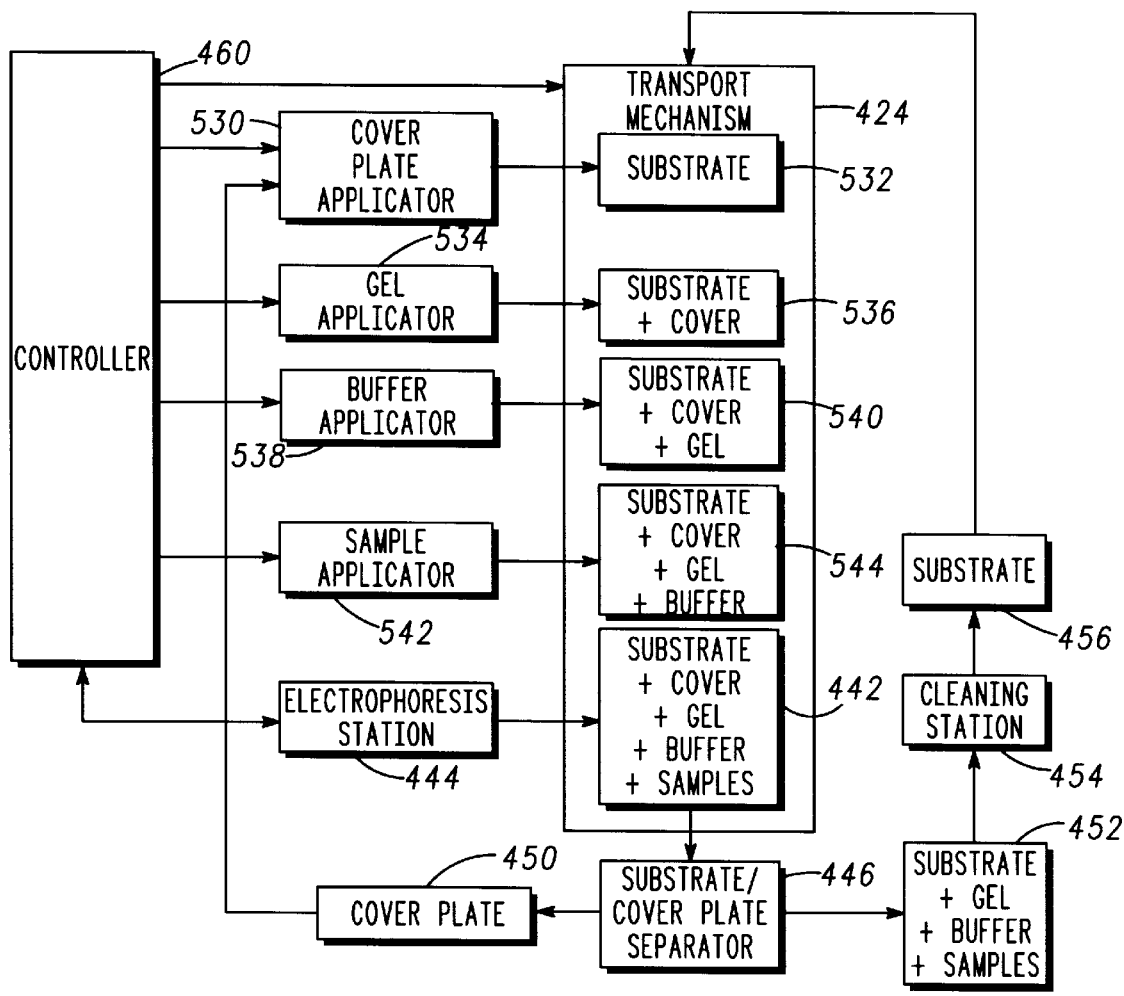
FIG. 23 is a block diagram of a second embodiment of an automated electrophoresis system in accordance with the present invention.

FIG. 23 is a block diagram of a second embodiment of an automated electrophoresis system in accordance with the present invention. This embodiment differs from the embodiment of FIG. 19 in that a cover plate applicator 530 applies a cover plate to a substrate 532 prior to receiving the gel, the buffer, and the sample.

A gel applicator 534 applies a gel to a substrate 536 having a cover plate. The gel applicator 534 can apply the gel at either end of a plurality of channels defined by the substrate. The gel can be drawn through the channels by applying a greater pressure at a gel-application end in comparison to a pressure at an opposite end. The greater pressure can be produced using a pump or the like. Alternatively, the gel can be drawn through the channels by applying a reduced pressure at an opposite end of the channels. The reduced pressure can be produced using a vacuum or the like applied to the opposite end.

A buffer applicator 538 applies a buffer to a substrate 540 having a cover plate and the gel. The buffer applicator 538 applies the buffer at either end of the channels. The buffer can be drawn through the channels using wicking devices as described earlier. Alternatively, the buffer can be drawn through the channels by pressurization.

A sample applicator 542 applies samples to a substrate 544 having a cover plate, the gel, and the buffer. The sample applicator 542 applies the samples at either end of the channels. Preferably, the samples are applied to one or more filling regions defined by the substrate 544.

The automated electrophoresis station further includes the electrophoresis station 444, the separator 446, the cleaning station 454, the controller 460, and the transport mechanism 424 described with reference to FIG. 19.

Thus, there has been described herein several embodiments including preferred embodiments of an electrophoresis apparatus and method.

Because the various embodiments of the present invention include a filling region having a greater dimension than the electrophoresis lanes, they provide a significant improvement in relaxing placement tolerances for applying samples thereto.

Additionally, the various embodiments of the present invention as herein-described provide an electrophoresis apparatus having electrophoresis lanes which can be individually loaded with samples, individually powered to electrophorese the samples, and can individually detect sample migration therein. Further, a statistical analysis of data obtained from a plurality of electrophoresis lanes in communication with the filling region can be performed to improve the confidence of sample molecule detection.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. An electrophoresis apparatus comprising:
a substrate;
a first filling region supported by the substrate;
a first plurality of electrophoresis lanes supported by the substrate, the first plurality of electrophoresis lanes in communication with the first filling region;
a second filling region supported by the substrate; and
a second plurality of electrophoresis lanes supported by the substrate, the second plurality of electrophoresis lanes in communication with the second filling region;
wherein the first plurality of electrophoresis lanes is adjacent the second plurality of electrophoresis lanes; and
wherein a distance between the first plurality of electrophoresis lanes and the second plurality of electrophoresis lanes is greater than a distance between each adjacent pair of the first plurality of electrophoresis lanes.

2. The electrophoresis apparatus of claim 1 further comprising at least one molecular sensor associated with the first plurality of electrophoresis lanes.

3. The electrophoresis apparatus of claim 2 wherein the at least one molecular sensor is integrated with the substrate.

4. The electrophoresis apparatus of claim 2 wherein the at least one molecular sensor includes a first electrode and a second electrode proximate to an electrophoresis lane of the first plurality of electrophoresis lanes.

5. The electrophoresis apparatus of claim 4 wherein the first electrode and the second electrode are located at opposite sides of the electrophoresis lane.

6. The electrophoresis apparatus of claim 5 further comprising a first insulating layer which insulates the first electrode from the electrophoresis lane and a second insulating layer which insulates the second electrode from the electrophoresis lane.

7. The electrophoresis apparatus of claim 5 wherein the first electrode and the second electrode abut with an interior portion of the electrophoresis lane.

8. The electrophoresis apparatus of claim 2 wherein the at least one molecular sensor includes a plurality of molecular sensors distributed along the electrophoresis lane.

9. The electrophoresis apparatus of claim 2 wherein the at least one molecular sensor includes a first molecular sensor and a second molecular sensor, the electrophoresis apparatus further comprising a bridge circuit which produces a signal based upon a difference between a first impedance sensed by the first molecular sensor and a second impedance sensed by the second molecular sensor.

10. The electrophoresis apparatus of claim 1 further comprising a plurality of molecular sensors, the plurality of molecular sensors including a respective molecular sensor for each of the first plurality of electrophoresis lanes.

11. The electrophoresis apparatus of claim 10 wherein the plurality of molecular sensors is integrated with the substrate.

12. The electrophoresis apparatus of claim 1 wherein the substrate defines a plurality of channels which provide the first plurality of electrophoresis lanes.

13. The electrophoresis apparatus of claim 12 wherein the plurality of channels are formed during molding of the substrate.

14. The electrophoresis apparatus of claim 12 wherein the plurality of channels are etched into the substrate.

15. The electrophoresis apparatus of claim 1 further comprising a heat sink integrated with the substrate, the heat sink to equalize temperatures of the first plurality of electrophoresis lanes with temperatures of the second plurality of electrophoresis lanes.

16. The electrophoresis apparatus of claim 15 wherein the heat sink is integrated with the substrate at an opposite face relative to a face at which the first plurality of electrophoresis lanes is supported.

17. The electrophoresis apparatus of claim 15 wherein the heat sink includes a thermoelectric member.

18. An electrophoresis apparatus comprising:

a substrate;

a plurality of electrophoresis lanes supported by the substrate;

a filling region supported by the substrate, the filling region having a sample-receiving opening at a first end and openings to the plurality of electrophoresis lanes at a second end;

wherein a dimension of the filling region is greater at the sample-receiving opening than at the openings to the plurality of electrophoresis lanes; and wherein an axis defined from the first end to the second end of the filling region is substantially parallel to the plurality of electrophoresis lanes.

19. An electrophoresis apparatus comprising:

a substrate;

a first filling region defined by the substrate, the first filling region having a first sample-receiving opening at a first sample-receiving end and a first plurality of openings at a first channel-opening end;

a first plurality of electrophoresis channels defined by the substrate, the first plurality of electrophoresis channels in communication with the first plurality of openings of the first filling region, the first plurality of electrophoresis channels substantially parallel to a first axis from the first sample-receiving end to the first channel-opening end of the first filling region;

a first plurality of molecular sensors including a respective molecular sensor for each of the first plurality of electrophoresis channels;

a second filling region defined by the substrate, the second filling region having a second sample-receiving opening at a second sample-receiving end and a second plurality of openings at a second channel-opening end;

a second plurality of electrophoresis channels defined by the substrate, the second plurality of electrophoresis channels in communication with the second plurality of openings of the second filling region, the second plurality of electrophoresis channels substantially parallel to a second axis from the second sample-receiving end to the second channel-opening end of the first filling region;

wherein the first plurality of electrophoresis channels is adjacent to the second plurality of electrophoresis channels, and a distance between the first plurality of electrophoresis channels and the second plurality of electrophoresis channels is greater than a distance between adjacent pairs of the first plurality of electrophoresis channels; and a second plurality of molecular sensors including a respective molecular sensor for each of the second plurality of electrophoresis channels.

20. A method of electrophoresis, the method comprising the steps of:

providing an electrophoresis device having a first filling region, a second filling region adjacent the first filling region, a first plurality of electrophoresis lanes in communication with the first filling region, and a second plurality of electrophoresis lanes in communication with the second filling region and adjacent the first plurality of electrophoresis lanes, wherein a distance between the first plurality of electrophoresis lanes and the second plurality of electrophoresis lanes is greater than a distance between each adjacent pair of the first plurality of electrophoresis lanes and each adjacent pair of the second plurality of electrophoresis lanes;

applying a first sample to the first filling region, the first plurality of electrophoresis lanes receiving the first sample from the first filling region;

applying a second sample to the second filling region, the second plurality of electrophoresis lanes receiving the second sample from the second filling region;

electrophoresing the first sample in the first plurality of electrophoresis lanes; and electrophoresing the second sample in the second plurality of electrophoresis lanes.

21. A method of electrophoresis, the method comprising the steps of:

providing an electrophoresis device having a filling region and a plurality of electrophoresis lanes in communication with the filling region, the filling region having a sample-receiving opening at a first end and openings to the plurality of electrophoresis lanes at a second end, wherein a dimension of the filling region is greater at the sample-receiving opening than at the openings to the plurality of electrophoresis lanes, and wherein an axis defined from the first end to the second end of the filling region is substantially parallel to the plurality of electrophoresis lanes;

applying a sample to the filling region, the plurality of electrophoresis lanes receiving the sample from the filling region; and electrophoresing the sample in the plurality of electrophoresis lanes.

* * * * *